(12) United States Patent
Cardosa

(10) Patent No.: US 10,125,187 B2
(45) Date of Patent: Nov. 13, 2018

(54) ANTIBODIES SPECIFIC FOR ENTEROVIRUSES THAT INFECT HUMANS

(71) Applicant: MAB Explorations Sdn Bhd, Georgetown (MY)

(72) Inventor: Mary Jane Cardosa, Georgetown (MY)

(73) Assignee: MAB Explorations Sdn Bhd, Georgetown (MY)

( * ) Notice: Subject to any disclaimer, the term of this patent is extended or adjusted under 35 U.S.C. 154(b) by 0 days.

(21) Appl. No.: 15/104,953

(22) PCT Filed: Dec. 16, 2014

(86) PCT No.: PCT/IB2014/066944
§ 371 (c)(1),
(2) Date: Jun. 15, 2016

(87) PCT Pub. No.: WO2015/092668
PCT Pub. Date: Jun. 25, 2015

(65) Prior Publication Data
US 2016/0333075 A1    Nov. 17, 2016

(30) Foreign Application Priority Data
Dec. 16, 2013 (MY) ............................ PI2013004513

(51) Int. Cl.
*A61K 39/42* (2006.01)
*C07K 16/10* (2006.01)
*C12N 5/16* (2006.01)

(52) U.S. Cl.
CPC .......... *C07K 16/1009* (2013.01); *C12N 5/163* (2013.01); *C07K 2317/14* (2013.01);
(Continued)

(58) Field of Classification Search
None
See application file for complete search history.

(56) References Cited

U.S. PATENT DOCUMENTS 7,932,099 B2    4/2011  Egan et al.
8,986,972 B2 *  3/2015  Stull ................ A61K 47/48638
                                                        424/130.1
(Continued)

FOREIGN PATENT DOCUMENTS

CN         102229915 A       11/2011
WO    WO-2004058191 A2 *    7/2004    ......... C07K 16/2878
(Continued)

OTHER PUBLICATIONS

Huang et al., "Seroprevalence of enterovirus 71 and no evidence of cross protection of enterovirus 71 antibody against the other enteroviruses in kindergarten children in Taipei city," Journal of Microbiology, Immunology and Infection 45: 96-101 (2012).*
(Continued)

*Primary Examiner* — Janet L Andres
*Assistant Examiner* — M Franco G Salvoza
(74) *Attorney, Agent, or Firm* — Seed IP Law Group LLP

(57) ABSTRACT

This invention provides antibodies or fragments thereof that are capable of specifically binding to at least one conformational epitope of enterovirus 71 (EV71), wherein the antibody individually comprises at least one variable light chain and at least one variable heavy chain. There is also provided a method of producing an antibody capable of specifically binding to at least one conformational epitope of enterovirus 71 (EV71).

9 Claims, 7 Drawing Sheets

Specification includes a Sequence Listing.

(52) U.S. Cl.
    CPC ...... *C07K 2317/24* (2013.01); *C07K 2317/34* (2013.01); *C07K 2317/76* (2013.01); *C07K 2317/90* (2013.01); *C07K 2317/92* (2013.01)

(56) References Cited

U.S. PATENT DOCUMENTS

| | | | |
|---|---|---|---|
| 2012/0070875 A1 | 3/2012 | Weisbart | |
| 2014/0127225 A1* | 5/2014 | Basi | C07K 16/18 424/145.1 |

FOREIGN PATENT DOCUMENTS

| | | |
|---|---|---|
| WO | 2010/062904 A2 | 6/2010 |
| WO | 2013/043125 A1 | 3/2013 |
| WO | 2013/098655 A2 | 7/2013 |

OTHER PUBLICATIONS

Rudikoff et al., "Single amino acid substitution altering antigen-binding specificity," Proc Natl Acad Sci USA 79:1979-1983 (1982).*

SEQ ID No. 1 NCBI Blast Search Result, database "pat" (2017).*
SEQ ID No. 15 NCBI Blast Search Result, database "pat" (2017).*
SEQ ID No. 2 NCBI Blast Search Result, database "pat" (2017).*
Ku et al., "Development of murine monoclonal antibodies with potent neutralization effects on enterovirus 71," *Journal of Virological Methods* 186:193-197, 2012.
Plevka et al., "Neutralizing antibodies can initiate genome release from human enterovirus 71," *PNAS* 111(6):2134-2139, 2014.
ShenJunZuo, "Preparation and identification of Anti-EV71 VP2 Monoclonal Antibody," Zheijiang University, Master's Thesis Dissertation, URL: http://www.dissertationtopic.net/doc/663943, Abstract, 2 pages, 2012.
Chang et al., "Protective Efficacy of VPI-Specific Neutralizing Antibody Associated with a Reduction of Viral Load and Pro-Inflammatory Cytokines in Human SCARB2-Transgenic Mice," *PLOS One* 8(7), 12 pages, 2013.
Kirk et al., "Cross-reactive neutralizing antibody epitopes against Enterovirus 71 identified by an in silico approach," *Vaccine* 30:7105-7110, 2012.
Lee et al., "A Strain-Specific Epitope of Enterovirus 71 Identified by Cryo-Electron Microscopy of the Complex with Fab from Neutralizing Antibody," *Journal of Virology*: 87(21):11363-11370, 2013.

* cited by examiner

ANTIBODIES SPECIFIC FOR ENTEROVIRUSES THAT INFECT HUMANS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 630246_401USPC_SEQUENCE_LISTING_ST25.txt. The text file is 25.7 KB, was created on Jun. 14, 2016, and is being submitted electronically via EFS-Web.

FIELD OF THE INVENTION

This invention is related to antibodies specific for enteroviruses that infect humans, method for producing the same, and uses thereof in treating human *enterovirus* infection, and as vaccine process controls to determine specificity and potency standards.

BACKGROUND OF THE INVENTION

Picornaviruses (Picornaviridae) are a diverse family of viruses which cause a number of common illnesses. Of the Picornaviridae family, viruses of the genus *Enterovirus* are significant for a number of diseases and affect millions of people worldwide each year. Nonspecific febrile illness is one of the most common presentations of an *enterovirus* infection. Other notable diseases caused by an *enterovirus* infection include poliomyelitis, pleurodynia, pericarditis, myocarditis, arrhythmias, myocardial infarction, and acute haemorrhagic conjunctivitis.

Viruses of the genus *Enterovirus* are often found in the respiratory secretions (e.g. saliva, sputum, or nasal mucus) and stool of an infected person. Historically, poliomyelitis, which is caused by the 3 polioviruses, was the most significant disease caused by an *enterovirus*. However, there are now close to a hundred non-polio enteroviruses that can cause diseases in humans; these include Coxsackie A viruses, Coxsackie B viruses, echoviruses, and many other *enteroviruses*. Excluding rhinoviruses, enteroviruses that cause human disease have recently been re-classified into 4 distinct species. Polioviruses and *enterovirus* 71 (EV71), like many other enteroviruses, are spread through the fecal-oral route. Infection can result in a wide variety of symptoms ranging from mild respiratory illness (common cold), hand, foot and mouth disease, acute hemorrhagic conjunctivitis, aseptic meningitis, myocarditis, severe neonatal sepsis-like disease, and acute flaccid paralysis.

*Enterovirus* infections are the most common causes of aseptic meningitis in children. In the United States, enteroviruses are responsible for 30,000 to 50,000 cases of meningitis. Further, a 2007 study suggested that acute respiratory or gastrointestinal infections associated with enteroviruses may be a factor in chronic fatigue syndrome.

Human *Enterovirus* 71 and Coxsackievirus A16 (CA16) are *enterovirus* serotypes in species A that are notable as the major causative agents for hand, foot and mouth disease (HFMD). The virus is excreted in faeces and is also found in pharyngeal secretions and blisters. Transmission is associated with close contact among children and through environmental contamination. The disease is characterized by an acute onset of fever with a rash on the palms, soles, buttocks, and knees, and vesicles on buccal membranes that usually resolves in 7-10 days. Only a small proportion of children with HFMD develop severe disease.

Some of the children infected by EV71 develop encephalitis, which is a rare manifestation of an *enterovirus* infection. Encephalitis may result in permanent brain damage and can be fatal. Severe disease involving primarily the neurologic and cardiovascular systems manifesting as syndromes such as meningitis, encephalitis, brainstem encephalitis, acute flaccid paralysis, pulmonary edema and cardiac failure generally occur only with EV71 infection. In the Asia-Pacific Region the most devastating neurological syndrome is brainstem encephalitis, which has a mortality rate of 40-80 percent. Children with severe HFMD may take months to recover, and in some cases the neurologic damage may be permanent. Currently, there is no specific antiviral treatment for HFMD and no vaccines to prevent *enterovirus* infection other than polio.

EV71 is additionally sometimes associated with severe central nervous system diseases. It was first isolated and characterized from cases of neurological disease in California in 1969. To date, little is known about the molecular mechanisms of host response to EV71 infection, but increases in the level of mRNAs encoding chemokines, proteins involved in protein degradation, complement proteins, and pro-apoptotic proteins have been implicated.

Although the virus has been detected worldwide since then, the recent regional epidemics of HFMD in Asia has raised concern that more pathogenic forms of EV71 may be emerging in the region. The first recognition of a HFMD outbreak with a high number of fatalities was in Sarawak, Malaysia in 1997. The virus associated with the outbreak then was EV71. Taiwan reported 129,106 HFMD cases in a 1998 epidemic with 405 having severe disease, and 78 deaths. Singapore reported an epidemic of 9000 cases with 7 deaths during 2000-2001, and since then has experienced recurrent epidemics every two to three years. During the first 8 months of 2008, Singapore reported 19,530 cases and one death due to HFMD. Since then EV71 outbreaks have been reported regularly in Singapore, Thailand, Malaysia, Taiwan, Japan, Korea, Vietnam, China, Australia and the Philippines.

China reported 83,344 cases with 17 deaths in 2007, and in 2008 experienced a large outbreak in Fuyang City in Anhui Province spreading throughout many parts of China. These large outbreaks were widely covered by the press, which highlighted parental concerns about the health of their children and the social disruption from closing of schools and day care centers by public health departments in an attempt to break the chain of transmission. Since then China has reported large outbreaks annually.

Monoclonal antibodies generated against peptides from EV71 capsid proteins generally have no or low neutralizing activity. Zhang et al., (2012) generated monoclonal antibodies against amino acid residues 94 to 97 which were reactive by western blotting, immunofluorescence and ELISA but could not neutralize EV71 virus. Kiener et al., (2012) described a monoclonal antibody against a VP2 capsid peptide (aa 142-146) which specifically reacts with EV71 but does not neutralize the virus. A commercially available monoclonal antibody MAB979 (Merck Millipore) which is reactive against a VP2 peptide (aa 141 to 150) (Liu et al., 2011) neutralizes the prototype EV71 (BrCr) at a titre of <1:14. Peptide SP55 (aa 163-177) which is within VP1 capsid and peptide SP70 (aa 208-222) also within VP1 generate monoclonal antibodies which either do not neutralize EV71 or do so at low titres such as 1:4 or 1:16 at best (Li et al., 2009). Lim et al., (2012) described 2 monoclonal antibodies generated to a peptide that is located within the SP70 peptide (Li et al., 2009) which share a common epitope KQEKD. One of the monoclonal antibodies neutralizes EV71 while the other does not. The authors suggest that the neutralization is dependent on antibody isotype, in this case, it is the antibody that has an IgM isotype that neutralizes while the IgG antibody does not. IgM has 10 binding sites while IgG has only 2, suggesting that the neutralizing activity is dependent on a blocking action of the antibody.

As the antibodies described above lack potency, there is a need to provide more effective monoclonal antibodies specific for EV71, and a method for producing potent neutralizing antibodies against EV71 and other picornaviruses. In addition, EV71 antibodies are needed for process controls and potency determination in EV71 vaccine development and would also be useful to help define EV71 antibody potency standards.

SUMMARY OF THE INVENTION

The current invention seeks to solve the problems above and provide antibodies specific for *enterovirus* 71 (EV71). According to a preferred aspect of the invention, there is provided at least one isolated antibody or a fragment thereof that is capable of specifically binding to at least one conformational (non-linear) epitope of EV71.

In a preferred embodiment, the antibody or fragment thereof may comprise at least one variable light chain amino acid sequence comprising SEQ ID NO: 1, a variant, mutant or fragment thereof, and at least one variable heavy chain amino acid sequence comprising SEQ ID NO: 2, a variant, mutant or fragment thereof.

In a preferred embodiment the antibody comprises a variable light chain comprising a sequence having at least 90% sequence identity to SEQ ID NO: 1 and a variable heavy chain comprising a sequence having at least 90% sequence identity to SEQ ID NO: 2.

In a preferred embodiment, the variable light chain amino acid sequence comprises SEQ ID NO: 15, a variant, mutant or fragment thereof.

According to another preferred embodiment, the antibody comprises at least one variable light chain and at least one variable heavy chain, wherein the variable light chain amino acid sequence comprises SEQ ID NO: 3, a variant, mutant or fragment thereof, and the heavy chain amino acid sequence comprises at least one of SEQ ID NOs: 4 and 5, a variant, mutant or fragment thereof.

In a preferred embodiment the antibody comprises a variable light chain comprising a sequence having at least 90% sequence identity to SEQ ID NO: 3 and a variable heavy chain comprising at least one sequence having at least 90% sequence identity to SEQ ID NO: 4 or 5.

In a preferred embodiment, the variable light chain amino acid sequence comprises at least one of SEQ ID NOs: 16, 17 and 18, a variant, mutant or fragment thereof, and the heavy chain amino acid sequence comprises at least one of SEQ ID NOs: 19, 20, 21 and 22, a variant, mutant or fragment thereof.

According to yet another preferred embodiment, the antibody comprises at least one variable light chain and at least one variable heavy chain, wherein the variable light chain comprises the amino acid sequence set forth in SEQ ID NO: 6, a variant, mutant or fragment thereof, and the heavy chain comprises the amino acid sequence set forth in SEQ ID NO: 7, a variant, mutant or fragment thereof.

In a preferred embodiment the antibody comprises a variable light chain comprising a sequence having at least 90% sequence identity to SEQ ID NO: 6 and a variable heavy chain comprising a sequence having at least 90% sequence identity to SEQ ID NO: 7.

In a preferred embodiment, the antibody or fragment thereof of the invention is a neutralizing antibody or fragment thereof.

In a preferred embodiment the antibody or fragment thereof of the invention is a monoclonal mouse, human, humanized or chimeric antibody.

According to another preferred aspect of the present invention, there is provided a method of producing an antibody specific for picornavirus, the method comprising:

immunizing at least one non-human mammal with at least one immature picornavirus particle to form at least one B cell specific for the picornavirus;

selecting at least one B cell specific to the picornavirus;

fusing the selected B cell with at least one immortalized cell to produce at least one hybridoma, wherein the hybridoma is capable of producing at least one antibody or a fragment thereof specific for the picornavirus; and optionally isolating the antibody from the hybridoma and sequencing the variable heavy and light chains.

According to another preferred aspect of the invention, there is provided an isolated nucleic acid molecule encoding (a) at least one variable light chain of the antibody or a fragment hereinbefore defined, wherein the variable light chain comprises at least one amino acid sequence selected from the group consisting of SEQ ID NOs: 3 and 16-18, a variant, mutant or fragment thereof; and/or (b) at least one variable heavy chain of the antibody or a fragment thereof hereinbefore defined, wherein the variable heavy chain comprises at least one amino acid sequence selected from the group consisting of SEQ ID NOs: 4, 5 and 19-22, a variant, mutant or fragment thereof.

In a preferred embodiment, the at least one nucleic acid sequence in (a) has at least 90% sequence identity to SEQ ID NO: 10 and/or 24 and/or 25 and/or26; and/or the at least one nucleic acid sequence in (b) has at least 90% sequence identity to SEQ ID NO: 11 and/or 12 and/or 27, and/or 28 and/or 29 and/or 30.

More preferably, the isolated nucleic acid molecule according to the above comprises:

(a) at least one nucleic acid sequence from the group consisting of SEQ ID NOs: 10 and 24-26, a mutant, variant or fragment thereof; and/or (b) at least one nucleic acid sequence from the group consisting of SEQ ID NOs: 11, 12, and 27-30, a mutant, variant or fragment thereof.

According to another embodiment of the invention there is provided an isolated nucleic acid molecule encoding (a) at least one variable light chain of the antibody or a fragment thereof, wherein the variable light chain comprises at least one amino acid sequence selected from the group consisting of SEQ ID NOs: 1 and 15, a variant, mutant or fragment thereof; and/or (b) at least one variable heavy chain of the antibody or a fragment thereof, wherein the variable heavy chain comprises at least one amino acid sequence of SEQ ID NO: 2, a variant, mutant or fragment thereof.

In one embodiment of the isolated nucleic acid molecule, the at least one nucleic acid sequence in (a) has at least 90% sequence identity to SEQ ID NO: 8 and/or 23; and/or the at least one nucleic acid sequence in (b) has at least 90% sequence identity to SEQ ID NO: 9.

More preferably, the isolated nucleic acid molecule comprises:
(a) at least one nucleic acid sequence of SEQ ID NO: 8 and/or 23, a mutant, variant or fragment thereof; and/or
(b) at least one nucleic acid sequence of SEQ ID NO: 9, a mutant, variant or fragment thereof.

According to another embodiment of the invention there is provided an isolated nucleic acid molecule encoding
(a) at least one variable light chain of the antibody or a fragment thereof, wherein the variable light chain comprises at least one amino acid sequence of SEQ ID NO: 6, a variant, mutant or fragment thereof; and/or
(b) at least one variable heavy chain of the antibody or a fragment thereof, wherein the variable heavy chain comprises at least one amino acid sequence of SEQ ID NO: 7, a variant, mutant or fragment thereof.

In one embodiment of the isolated nucleic acid molecule, the at least one nucleic acid sequence in (a) has at least 90% sequence identity to SEQ ID NO: 13; and/or
the at least one nucleic acid sequence in (b) has at least 90% sequence identity to SEQ ID NO: 14.

More preferably, the isolated nucleic acid molecule comprises:
(a) at least one nucleic acid sequence of SEQ ID NO: 13, a mutant, variant or fragment thereof; and/or
(b) at least one nucleic acid sequence of SEQ ID NO: 14, a mutant, variant or fragment thereof.

According to a further preferred aspect of the invention, there is provided at least one conformational epitope of EV71, wherein the conformational epitope is capable of being recognized by at least one antibody according to any aspect of the present invention.

According to other preferred aspects, the present invention provides a method for characterizing at least one conformational neutralizing epitope on a potential *enterovirus* vaccine candidate and a method for purifying a potential *enterovirus* vaccine candidate that contains at least one conformational epitope.

Further, a preferred embodiment of the present invention provides a method to define the neutralizing antibody potency for EV71 and EV71 vaccines. The antibody of the invention may also be used for EV71 vaccine process control.

According to other preferred aspects, the present invention provides a method of treating EV71 and/or at least one EV71-linked disease; the antibody or fragment thereof of the present invention for use as medicine; use of the antibody or fragment thereof of the present invention for the preparation of a medicament; kits comprising the antibody or fragment thereof of the invention, nucleic acids and uses thereof; an expression vector comprising at least one of the isolated nucleic acids of the invention; a host cell comprising the expression vector of the invention, as well as a conformational epitope capable of being recognized by at least one antibody according to any aspect of the present invention.

As will be apparent from the following description, preferred embodiments of the present invention allow an optimal use of the isolated antibodies to take advantage of their accuracy and specificity to at least one epitope of EV71. This and other related advantages will be apparent to skilled persons from the description below.

BRIEF DESCRIPTION OF THE FIGURES

FIG. 6A also demonstrates by Western blot that EV71 virus-like particles can be purified using an antibody E18 affinity column. Furthermore, affinity columns prepared with E18 and E19 can also purify infectious virions (FIG. 6A)

DETAILED DESCRIPTION OF THE INVENTION

Figure 1A:
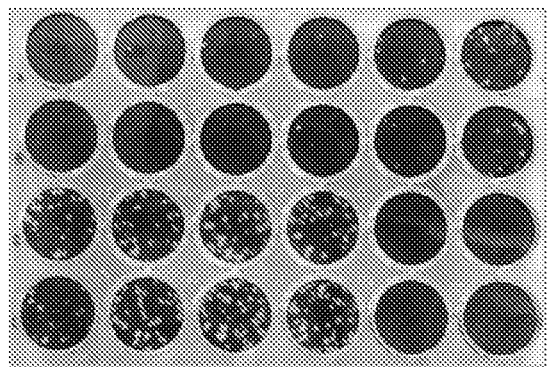
FIG. 1 shows images of 24-well plates showing results of the plaque reduction neutralization test (PRNT) for antibodies E18 (A), E19 (B), and E20 (C).

Bibliographic references mentioned in the present specification are for convenience listed in the form of a list of references and added at the end of the examples. The whole content of such bibliographic references is herein incorporated by reference.

Definitions

For convenience, certain terms employed in the specification, examples and appended claims are collected here.

As used herein, the term "antibody" refers to any immunoglobulin or intact molecule as well as to fragments thereof that bind to a specific epitope. Such antibodies include, but are not limited to polyclonal, monoclonal, chimeric, humanised, single chain, single chain fragment variable (scFv), Fab, Fab', F(ab)' fragments and/or F(v) portions of the whole antibody. The term "monoclonal antibody" may be referred to as "Mab". The antibody includes antibodies E18, E19, and E20, produced by the hybridoma cell lines EV18/4, EV19/5, and EV20/5, respectively. The antibodies, E18, E19 and E20 may be monoclonal antibodies, polyclonal antibodies, single-chain antibodies, and fragments thereof which retain the antigen binding function of the parent antibody. The antibodies E18, E19, and E20 are capable of specifically binding to EV71, including but not limited to a conformational epitope comprising at least one capsid protein of EV71 and include monoclonal antibodies, polyclonal antibodies, single-chain antibodies, and fragments thereof which retain the antigen binding function of the parent antibody.

The term "antibody fragment" as used herein refers to an incomplete or isolated portion of the full sequence of the antibody which retains the antigen binding function of the parent antibody. Examples of antibody fragments include scFv, Fab, Fab', F(ab')2, and Fv fragments; diabodies; linear antibodies; single-chain antibody molecules; and multi-specific antibodies formed from antibody fragments. Fragments of the E18, E19, and E20 antibodies are encompassed by the invention so long as they retain the desired affinity of the full-length antibody. In particular, it may be shorter by at least one amino acid. A single chain antibody may, for example, have a conformation comprising SEQ ID NO: 1 and SEQ ID NO: 2 with a linker positioned between them. Another combination may be SEQ ID NO: 15 and SEQ ID NO: 2 in single chain configuration.

The term "antigen" as used herein, refers to a substance that prompts the generation of antibodies and can cause an immune response. It may be used interchangeably in the present invention with the term "immunogen". In the strict sense, immunogens are those substances that elicit a response from the immune system, whereas antigens are defined as substances that bind to specific antibodies. An antigen or fragment thereof may be a molecule (i.e. an epitope) that makes contact with a particular antibody. When a protein or a fragment of a protein is used to immunize a host animal, numerous regions of the protein may induce the production of antibodies (i.e. elicit the immune response), which bind specifically to the antigen (given regions or three-dimensional structures on the protein). Non-limiting examples of an antigen is the VP0 protein of EV71 and an immature picornavirus particle. The antigen may include but is not limited to a capsid protein and/or non-structural proteins of EV71. In particular, the term "epitope" may refer to a consecutive sequence of from about 5 to about 13 amino acids which form an antibody binding site. The epitope in the form that binds to the antibodies or binding protein may be a denatured protein that is substantially devoid of tertiary structure. The epitope may be a conformational epitope that comprises non-consecutive elements from non-consecutive sequences. The epitope may also be a quaternary epitope which comprises non-consecutive elements from more than one protein or polypeptide which are assembled into a particle such as a VLP, a virion or an assembly of some other kind.

A "conformational epitope" is herein defined as a sequence of subunits (usually, amino acids) comprising an antigen that comes in direct contact with the Variable Light and Heavy chains of an antibody. Whenever an antibody interacts with an undigested antigen, the surface amino acids that come in contact may not be continuous with each other if the protein is unwound. Such discontinuous amino acids that come together in three dimensional conformation and interact with the antibody's paratope are called conformational epitopes. In contrast, if the antigen is digested, small segments called peptides are formed, which bind with major histocompatibility complex molecules, and then later with T cell receptors through amino acids that are continuous in a line. These are known as linear epitopes.

The term "comprising" is herein defined to be that where the various components, ingredients, or steps, can be conjointly employed in practicing the present invention. Accordingly, the term "comprising" encompasses the more restrictive terms "consisting essentially of" and "consisting of."

The term "chimeric antibody," as used herein, refers to at least one antibody molecule in which the amino acid sequence in the constant regions has been altered so that the antibody more closely resembles a human antibody, and still retains its original binding ability.

The term "humanized antibody", as used herein, refers to at least one antibody molecule in which the amino acid sequence within the variable and constant regions has been altered so that the antibody more closely resembles a human antibody, and still retains its original binding ability. As used herein, the term "hybridoma" refers to cells that have been engineered to produce a desired antibody in large amounts. For example, to produce at least one hybridoma, B cells are removed from the spleen of an animal that has been challenged with the relevant antigen and fused with at least one immortalized cell. This fusion is performed by making the cell membranes more permeable. The fused hybrid cells (called hybridomas), will multiply rapidly and indefinitely and will produce at least one antibody. Examples of hybridomas are the cell lines EV18/4, EV19/5, and EV20/5.

"Immortalised cells" as used herein are also known as transformed cells—i.e. cells whose growth properties have been altered. This does not necessarily mean that these are "cancer" or "tumour" cells, i.e. able to form a tumour if introduced into an experimental animal, although in some cases they may do. Immortalised cell lines include but are not limited to NS1, Jurkat, HeLa, HepG2, SP2/0, Hep-3b and the like.

The term "immunological binding characteristics" of an antibody or related binding protein, in all of its grammatical forms, refers to the specificity, affinity and cross-reactivity of the antibody or binding protein for its antigen.

The term "isolated" is herein defined as a biological component (such as a nucleic acid, peptide or protein) that has been substantially separated, produced apart from, or purified away from other biological components in the cell of the organism in which the component naturally occurs, i.e., other chromosomal and extra-chromosomal DNA and RNA, and proteins. Nucleic acids, peptides and proteins which have been isolated thus include nucleic acids and proteins purified by standard purification methods. The term also embraces nucleic acids, peptides and proteins prepared by recombinant expression in a host cell as well as chemically synthesized nucleic acids.

The term "neutralising antibody" is herein defined as an antibody that can neutralise the ability of that pathogen to initiate and/or perpetuate an infection in a host. The invention provides at least one neutralising human monoclonal antibody, wherein the antibody recognises an antigen from EV71.

The term "framework" is herein defined as the region of an antibody that provides structural support for function but does not directly bind the epitope.

The term "mutant" is herein defined as one which has at least one nucleotide sequence that varies from a reference sequence via substitution, deletion or addition of at least one nucleic acid, but encodes an amino acid sequence that retains the ability to recognize and bind the same conformational epitope on EV71 as the un-mutated sequence encodes. The term 'mutant' also applies to an amino acid sequence that varies from at least one reference sequence via substitution, deletion or addition of at least one amino acid, but retains the ability to recognize and bind the same conformational epitope on EV71 as the un-mutated sequence. In particular, the mutants may be naturally occurring or may be recombinantly or synthetically produced. More in particular, the mutant may be of at least 50%, at least 60%, at least 70%, at least 80%, at least 90%, or at least 95% sequence identity to the reference sequences. For example, the E18 variable light chain amino acid sequence set forth in SEQ ID NO: 15 is shorter than the sequence set forth in SEQ ID NO: 1 and may be considered a mutant of SEQ ID NO: 1 because it retains the ability to recognize and bind the same conformational epitope on EV71. Likewise, the humanized E19 variable light chain amino acid sequence set forth in SEQ ID NO: 16 was created by substituting amino acids in the E19 variable light chain amino acid sequence set forth in SEQ ID NO: 3 with preferred human framework and may be considered a mutant of SEQ ID NO: 3.

The term "variant" as used herein, refers to an amino acid sequence that is altered by one or more amino acids, but retains the ability to recognize and bind the same conformational epitope on EV71 as the non-variant reference sequence. The variant may have "conservative" changes, wherein a substituted amino acid has similar structural or chemical properties (e.g., replacement of leucine with isoleucine). More rarely, a variant may have "non-conservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR® software (DNASTAR, Inc. Madison, Wis., USA). For example, the E18 variable light chain amino acid sequence set forth in SEQ ID NO: 15 is shorter than the sequence set forth in SEQ ID NO: 1 and may be considered a variant of SEQ ID NO: 1 because it retains the ability to recognize and bind the same conformational epitope on EV71. Likewise, the humanized E19 variable light chain amino acid sequence set forth in SEQ ID NO: 16 was created by substituting amino acids in the E19 variable light chain amino acid sequence set forth in SEQ ID NO: 3 with preferred human framework and may be considered a variant of SEQ ID NO: 3.

The term "sample," as used herein, is used in its broadest sense. A biological sample suspected of containing nucleic acids encoding at least one EV71 derived peptide, or fragments thereof, or EV71 itself may comprise a bodily fluid, an extract from a cell, chromosome, organelle, or membrane isolated from a cell, a cell; genomic DNA, RNA, or cDNA (in solution or bound to a solid support), a tissue, a tissue print and the like.

As used herein, the terms "specific binding" or "specifically binding" refer to the interaction between one or more proteins or peptides and an agonist, an antibody, or an antagonist. In particular, the binding is between an antigen and an antibody. The interaction is dependent upon the presence of a particular structure of the one or more proteins recognized by the binding molecule (i.e., the antigen or epitope). As described hereinbefore, the antigen or epitope may be comprised of more than a single peptide sequence from the same protein or different proteins which come together spatially to form a conformational antigen or epitope. For example, if an antibody is specific for epitope "A", the presence of a polypeptide containing the epitope A, or the presence of free unlabeled A, in a reaction containing free labeled A and the antibody will reduce the amount of labeled A that binds to the antibody.

The term "immature picornavirus particle" refers to an empty virus particle which lacks the genome materials and comprises the capsid proteins VP0, VP1 and VP3. Capsid protein V0 is a precursor of the capsid proteins V2 and V4.

The term "treatment", as used in the context of the invention refers to prophylactic, ameliorating, therapeutic or curative treatment.

The term "subject" is herein defined as vertebrate, particularly mammal, more particularly human. For purposes of research, the subject may particularly be at least one animal model, e.g., a mouse, rat and the like. In particular, for treatment of EV-71 infection and/or EV71-linked diseases, the subject may be a human infected by EV71.

A person skilled in the art will appreciate that the present invention may be practiced without undue experimentation according to the method given herein. The methods, techniques and chemicals are as described in the references given or from protocols in standard biotechnology and molecular biology text books.

According to a preferred aspect, the present invention provides isolated monoclonal antibodies and related binding proteins that bind specifically to EV71. The antibodies according to any aspect of the present invention may be monoclonal antibodies (Mab) which may be a substantially homogeneous population of antibodies derivable from a single antibody-producing cell. Thus, all antibodies in the population may be identical and may have the same specificity for a given epitope. The specificity of the Mab responses provides a basis for an effective treatment against EV71 infection and/or at least one EV71-linked disease. Monoclonal antibodies and binding proteins derived therefrom also have utility as therapeutic agents.

The antibodies according to any aspect of the present application provide at least one anti-EV71 antibody which is capable of neutralizing EV71 infection and inhibiting cell-to-cell spread. These antibodies according to any aspect of the present application may be used as prophylactic and/or therapeutic agent(s) for the treatment of EV71 and EV71-linked diseases.

According to a preferred embodiment of the present invention, there is provided an isolated antibody or a fragment thereof that is capable of specifically binding to at least one conformational epitope of *enterovirus* 71 (EV71).

In particular, the isolated antibody may be selected from the group consisting of:
(a) an antibody produced by hybridoma cell line EV18/4;
(b) an antibody having the binding characteristics of the antibody produced by hybridoma cell line EV18/4;
(c) an antibody that binds to an antigen capable of binding to the antibody produced by hybridoma cell line EV18/4;
(d) an antibody comprising at least one variable light chain and at least one variable heavy chain, wherein the variable light chain comprises SEQ ID NO: 1, a variant, mutant or fragment thereof, and the variable heavy chain comprises SEQ ID NO: 2, a variant, mutant, or fragment thereof.

The isolated monoclonal antibody or a fragment thereof may be a neutralizing monoclonal antibody or a fragment thereof that may be capable of specifically binding to at least one epitope of EV71. The epitope may be a linear one or may be a conformational epitope. The conformational epitope may be on an intact virus capsid. More in particular, the epitope may comprise one or more of the capsid proteins VP1, VP2 VP3, VP4 and/or VP0 precursor. All members of the genus *Enterovirus*, including EV71, poliovirus and Coxsackievirus A16 have a single stranded positive sense RNA genome which has a single open reading frame encoding a polyprotein, P1, consisting of the capsid proteins, VP4, VP2, VP3 and VP1, and several non-structural proteins including the viral proteases 3C and 3CD which are responsible for cleaving the polyprotein P1 into individual capsid proteins VP1, VP3 and VP0. VP0 is a precursor of VP2 and VP4. The capsid proteins may assemble into virus like particles (VLPs).

The inventors of the present application showed that antibodies capable of neutralizing EV71 may be generated by using an immature EV71 virus particle as an antigen. In particular, the immature EV71 virus particle may be an empty virus particle which does not contain the genome materials. More in particular, the immature EV71 virus particle may comprise the capsid protein VP0.

Like all enteroviruses, four different capsid polypeptides have been identified and are designated as VP1, VP2, VP3, and VP4, which associate to form an icosahedral virus capsid. Typically, vaccination with the individual polypeptides of polioviruses has shown that the isolated polypeptides or peptides are not capable of raising potent neutralizing antibodies in humans and animals. The isolated monoclonal antibody of fragment thereof of the invention is not only neutralizing but also induces early genome release which is a novel mechanism by which antibodies can neutralize viruses. Furthermore, the approach presented in this application may be used to prepare antibodies with similar properties against related viruses that include significant human pathogens.

The antibody according to a preferred embodiment of the present invention may be produced by the hybridoma cell line, EV18/4 or by standard recombinant methods, and may comprise at least one variable light (VL) chain comprising SEQ ID NO: 1 as shown in Table 1, or a variant, mutant, or fragment thereof, and/or at least one variable heavy (VH) chain comprising SEQ ID NO: 2 as shown in Table 1, or a variant, mutant or fragment thereof. In particular, the isolated antibody may comprise at least one variable light chain comprising a sequence having at least 80%, at least 90% or at least 95% sequence identity to SEQ ID NO: 1, and/or at least one variable heavy chain comprising at least one a sequence having at least 80% at least 90%, or at least 95% sequence identity to SEQ ID NO: 2.

TABLE 1

Polypeptide sequences of the antibodies produced by the hybridoma cell lines EV18/4, E19/5, or E20/5.

| SEQ ID NO. | Hybridoma | Chain | Sequences |
|---|---|---|---|
| 1 | EV18/4 | VL | DIKMTQSPSSMYASLGERVTITCKASQDIKS YLSWYQQKPWKSPKTLIYYAKNLADGVPSRF SGSGFGQDYSLTISSLESDDTATYYCLQHGE SPYTFGSGTKLEIKR |
| 2 | | VH | QIQLVQSGPELKKPGETVKISCKASGYTFTR YGMSWVKQAPGKGLKWMGWINTYSGVPTYAD DFKGRFAFSLETSASTAYLQINNLKNEDTAT YFCARRGYSNYYPMDFWGQGTSVTVSS |
| 3 | E19/5 | VL | NIMMTQSPSSLAVSAGGKVTMSCKSSQSVLY SSNQKNYLAWYQQKPGQSPKLLIYWASTRES GVPDRFTGSGSGTDFTLTISSVQAEDLAVYY CHQYLSSWTFGGGTKLEIK |
| 4 | | VH1 | EVMLVESGGGLVKPGGSLQLSCAASGFTFSD YAMSWVRQTAETRLEWVATISDGGSHTYYPD SVRGRFTISRDNAKKALYLEMSSLKSEDTAM YYCGRRAGRYDERDAMDYWGQGTTVTVSS |

TABLE 1 -continued

Polypeptide sequences of the antibodies produced by the hybridoma cell lines EV18/4, E19/5, or E20/5.

| SEQ ID NO. | Hybridoma | Chain | Sequences |
|---|---|---|---|
| 5 | | VH2 | SDVQLQESGPGLVKPSQSLSLICSVTGYSIT SGFYLNWIRQFPGNKLEWMGYINYGGSINYN PSLKSRISITRDTSKNQFFLRLNSVTAEDTA TYYCATMPNSWYFDVWGTGTTVTVSS |
| 6 | E20/5 | VL | SIVMTQTPKFLPVSAGDRVTMTCKASQSVGN NVAWYQQKSGQSPKLLIYYASNRYTGVPDRF TGSGSGTDFTFTISSVQVEDLAVYFCQQHYS SPPTFGAGTKLELK |
| 7 | | VH | EVQLVESGGGLVKPGGSLKLSCAASGFTFNI YAMSWVRQTPEKRLEWVATISDGGSYTYYPD NVKGRFTISRDNAKNNLYLQMSHLKSEDTAM YYCVRDRGNYYSRAFPYAYWGQGTLVTVSA |

According to another preferred embodiment of the invention, there is provided an isolated antibody or a fragment thereof that is capable of specifically binding to at least one epitope of *Enterovirus* 71 (EV71), wherein the antibody is selected from the group consisting of:

(a) an antibody produced by a hybridoma cell line EV19/5;

(b) an antibody having the binding characteristics of the antibody produced by the hybridoma cell line EV19/5;

(c) an antibody that binds to an antigen capable of binding to the antibody produced by the hybridoma cell line EV19/5;

(d) an antibody comprising at least one variable light chain and at least one variable heavy chain, wherein the variable light chain comprises SEQ ID NO: 3 as set out in Table 1, a variant, mutant or fragment thereof, and the variable heavy chain comprises at least one of SEQ ID NOs: 4 and 5 as set out in Table 1, a variant, mutant or fragment thereof.

In particular, the isolated antibody may comprise a variable light chain comprising a sequence having at least 80%, at least 90% or at least 95% sequence identity to SEQ ID NO: 3, and/or at least one variable heavy chain comprising at least one sequence having at least 80%, at least 90%, or at least 95% sequence identity to SEQ ID NOs: 4 or 5.

According to another preferred embodiment of the invention, there is provided an isolated antibody or a fragment thereof that is capable of specifically binding to at least one conformational epitope of *Enterovirus* 71 (EV71), wherein the antibody is selected from the group consisting of:

(a) an antibody produced by a hybridoma cell line EV20/5;

(b) an antibody having the binding characteristics of the antibody produced by the hybridoma cell line EV20/5;

(c) an antibody that binds to an antigen capable of binding to the antibody produced by the hybridoma cell line EV20/5;

(d) an antibody comprising at least one variable light chain and at least one variable heavy chain, wherein the variable light chain comprises SEQ ID NO: 6, a variant, mutant or fragment thereof, and the variable heavy chain comprises SEQ ID NO: 7, a variant, mutant or fragment thereof.

In particular, the isolated antibody may comprise a variable light chain comprising a sequence having at least 80%, at least 90% or at least 95% sequence identity to SEQ ID NO: 6, and/or at least one variable heavy chain comprising a sequence having at least 80%, at least 90%, or at least 95% sequence identity to SEQ ID NO: 7.

The antibodies, E18, E19, and E20 may be capable of blocking viral mechanisms to spread within a host. They effectively neutralize cell-free virus particles and inhibit the direct cell-to-cell spread of the virus.

The antibodies according to any embodiments of this invention bind to at least one conformational epitope of EV71. This is advantageous as epitopes usually exist in nature in a three dimensional conformation and the antibodies may thus be more efficient and effective in detecting the presence of EV71 and/or subsequently neutralizing the effect of EV71. The conformational epitope may comprise at least one capsid protein and/or at least one non-structural protein. The capsid protein may be an intact virus capsid protein. The capsid protein may comprise one or more proteins selected from the group consisting of VP1, VP2 VP3, VP4 and VP0 precursor. The antibodies according to any aspect of the present invention may be capable of recognizing a whole spectrum of EV71 viruses. These antibodies may be of high specificity and sensitivity. The antibodies of the present invention provide several advantages, including being capable of use as drugs or vaccines for HFMD.

In particular, the antibodies according to any aspect of the present invention may be available in large quantities, prepared either in hybridoma supernatant, ascites fluid or recombinant bacteria or plant and/or animal cells. There may also be a constant and renewable source of monoclonal antibodies available, with any one of the hybridoma cell lines according to any aspect of the present invention. These antibodies may also be easily purified by affinity chromatography, using any method known in the art. The defined epitope recognized by the antibodies according to any aspect of the present invention also allows for mechanistic study of the antibody's virus neutralization ability to be easily performed.

In one embodiment, the neutralizing antibodies according to any aspect of the present invention may be capable of effective in vivo protection against EV71 infection. The efficacy and specificity of these antibodies are shown in the Examples.

In particular, the antibody according to any aspect of the present invention may comprise the immunological binding characteristics of the monoclonal antibody E18, E19 or E20. The immunological binding characteristics of E18 are produced by hybridoma EV18/4. The immunological binding characteristics of E19 are produced by hybridoma EV19/5. The immunological binding characteristics of E20 are produced by hybridoma EV20/5. The hybridomas provide a continuous source of the antibodies and binding proteins of the invention. The sequences provide a means to recombinantly recreate each antibody as well.

According to another aspect of the invention, there is provided a method for producing an antibody specific for picornavirus, the method comprising immunizing at least one non-human mammal with at least one immature picornavirus particle to form at least one B cell specific for the picornavirus, and selecting at least one immune B cell specific to the picornavirus. In particular, the non-human animal may be a mouse. More in particular, the non-human mammal may be a Balb/c mouse.

In particular, an immature picornavirus particle may be an empty picornavirus particle which does not contain the genome material. The immature picornavirus particle may contain the capsid proteins VP1, VP3, VP0 and/or VP2 and VP4. More in particular, the immature picornavirus particle may contain the capsid protein VP2 and/or VP4 or VP0, which is a precursor of the capsid proteins V2 and V4. The empty particles are presumably precursors of the mature infectious virions.

Antibodies may be obtained by fusing the immune B-cells from the spleen of a non-human mammal with an immortal cell line to produce a hybridoma cell line. The hybridoma cell line may secrete a single type of monoclonal antibody that has precise specificity and often high affinity against the picornavirus. In particular, the immortal cell line may be "cancer" or "tumour" cells. More in particular, the immortal cell line may include but are not limited to NS1, Jurkat, HeLa, HepG2, SP2/0, Hep-3b and the like. The antibody may be isolated from the hybridoma and the variable heavy and light chains sequenced.

The picornavirus family encompasses the following genuses: *Aphthovirus, Aquamavirus, Avihepatovirus, Cardiovirus, Cosavirus, Dicipivirus, Enterovirus, Erbovirus, Hepatovirus, Kobuvirus, Megrivirus, Parechovirus, Salivirus, Sapelovirus, Senecavirus, Teschovirus,* and *Tremovirus.* In particular, the picornavirus may be from the genus *Enterovirus.* More in particular, the picornavirus may be enterovirus 71 (EV71).

*Enterovirus* represents a genus of a large and diverse group of small RNA viruses characterized by a single positive-strand genomic RNA. All enteroviruses contain a genome of approximately 7,500 bases and are known to have a high mutation rate due to low-fidelity replication and frequent recombination. After infection to the host cell, the genome is translated in a cap-independent manner into a single polyprotein, which is subsequently processed by virus-encoded proteases into the structural capsid proteins and the non-structural proteins, which are mainly involved in the replication of the virus.

Serological studies have distinguished around a hundred human *enterovirus* serotypes on the basis of antibody neutralization tests and genomic information. Additional antigenic variants have been defined within several of the serotypes on the basis of reduced or nonreciprocal cross-neutralization between variant strains. On the basis of their pathogenesis in human and animals, enteroviruses were originally classified into four groups, polioviruses Coxsackie A viruses (CA), Coxsackie B viruses (CB), and echoviruses. However it was quickly realized that there were significant overlaps in the biological properties of the viruses that cause human disease and they have now been reclassified into 4 genetic clusters, excluding rhinoviruses. Table 2 shows the species and serotypes encompassed by the *Enterovirus* genus.

TABLE 2

Species and serotypes of *Enterovirus*.

| Species | Serotypes |
|---|---|
| Human *enterovirus* A | Baboon Enterovirus, Coxsackicevirus A10, A12, A14, A16, A2-8, Enterovirus A71, A76, A89, A90, A91, A92, Simian enterovirus 19, 43, 46 |
| Human *enterovirus* B | E1-9, E11-21, E24-33, , Enterovirus B69, B73-75, B77-80, , B83-87, B97, Enterovirus Yanbian 96-83csf, Enterovirus Yanbian 96-85csf, Simian agent 5, Human enterovirus 100, 101, 107, 79, 81, 82, 88, 93, 95 and 98 |
| Human *enterovirus* C | Coxsackievirus A1, A11, A13, A17, A19, A20, Enterovirus C95, C99, Human coxsackievirus A15, A18, A19/22, A22, Human enterovirus C104, C105, C109, C116, C96, wild poliovirus type 3, unidentified poliovirus |

TABLE 2-continued

Species and serotypes of Enterovirus.

| Species | Serotypes |
|---|---|
| Human enterovirus D | Enterovirus D68, Human enterovirus 70, Human enterovirus 94, Human enterovirus D111 |
| Human enterovirus E | Bovine enterovirus strain K2577, SL305, VG-5-27, and type 1 |
| Human enterovirus F | Bovine enterovirus type 2 |
| Human enterovirus G | Ovine enterovirus, Porcine enterovirus 10, 15, 3H, 9, J10 |
| Human enterovirus H | A-2 plague virus, Simian enterovirus SA4, Human enterovirus 101, 107, 79, 81, 82, 88, 93, 95, 98, Simian agent 5 |
| Human enterovirus J | SV6, EV-J103, EV-J108, EV-J112, EV-J115 and EV-J121 |
| Human rhinovirus A | Human Rhino Virus (HRV) A1, A2, A7-13, A15, A16, A18, A19, A20-25, A28-34, A36, A38, A39, A40, A41, A43, A44-47, A49, A50, A51, A53-68, A71, A73-78, A80, A81, A82, A85, A88, A89, A90, A94, A95, A96, A98 |
| Human rhinovirus B | human rhinovirus (HRV) B3, B4, B5, B6, B14, B17, B26, B27, B35, B37, B42, B48, B52, B69, B70, B72, B79, B83, B84, B86, B91, B92, B93, B97 and B99 |
| Human rhinovirus C | human rhinovirus (HRV) C1-3, C5-C12, C15, C17, C18, C19, C20, C22, C25, C28, C32, C35, C36, C37, C39, C40, C42, C43, C49, C |

The antibodies of the present invention may be produced by any technique that provides for the production of antibody molecules by continuous cell lines in culture. Such methods include, but are not limited to, the hybridoma technique originally developed in 1975 by Kohler and Milstein, as well as the trioma technique, the human B-cell hybridoma technique and the EBV-hybridoma technique to produce human monoclonal antibodies (Cole et al., 1985). Human antibodies can be used and can be obtained by using human hybridomas (Cote et al., 1983). Additionally, once antibody sequences are known production can be achieved using standard recombinant technologies well known in the art.

According to an aspect of the present invention, there is provided an isolated nucleic acid molecule encoding at least one variable light chain of an antibody according to any aspect of the present invention, or a variant, mutant, or fragment thereof, and at least one variable heavy chain of an antibody according to any aspect of the present invention, or a variant, mutant, or fragment thereof. In particular, the isolated nucleic acid molecule may encode at least one of SEQ ID NOs: 1, 3 and 6, a variant, mutant, or fragment thereof and at least one of SEQ ID NOs: 2, 4, 5 and 7, a variant, mutant or fragment thereof. More in particular, the isolated nucleic acid molecule may comprise at least one of SEQ ID NOs: 8, 10, and 13, a variant, mutant, or fragment thereof and at least one of SEQ ID NOs: 9, 11, 12, and 14, a variant, mutant, or fragment thereof as listed in Table 3.

TABLE 3

Nucleic acid sequences encoding for the variable light chain or variable heavy chains of antibodies EV18, 19 and 20.

| SEQ ID No. | Hybridoma | Chain | Sequences |
|---|---|---|---|
| 8 | EV18/4 | VL | GACATCAAGATGACCCAGTCTCCATCCTCCATGTATGCATCGCTGGGAGAGAGA GTCACTATCACTTGCAAGGCGAGTCAGGACATTAAAAGCTATTTAAGCTGGTACC AGCAGAAACCATGGAAATCTCCTAAGACCCTGATCTATTATGCAAAAAACTTGGC AGATGGGGTCCCATCAAGATTCAGTGGCAGTGGATTTGGGCAAGATTATTCTCTA ACCATCAGCAGCCTGGAGTCTGACGATACAGCAACTTATTACTGTCTACAGCATG GTGAGAGCCCGTATACGTTCGGATCGGGGACCAAACTGGAAATAAAACGG |
| 9 | | VH | CAGATCCAGTTGGTACAGTCTGGACCTGAGCTGAAGAAGCCTGGAGAGACAGTC AAGATCTCCTGCAAGGCTTCTGGATATACCTTCACAAGGTATGGAATGAGCTGG GTGAAACAGGCTCCAGGAAAGGGTTTAAAGTGGATGGGCTGGATAAACACCTAC TCTGGAGTGCCAACATATGCTGACGACTTCAAGGGACGGTTTGCCTTCTCTTTGG AAACCTCTGCCAGCACTGCCTATTTGCAGATCAACAACCTCAAAAATGAGGACAC GGCTACATATTTCTGTGCAAGAAGGGGGTATAGTAACTATTATCCTATGGACTTC TGGGGTCAAGGAACCTCAGTCACCGTCTCCTCA |
| 10 | E19/5 | VL | AACATTATGATGACACAGTCGCCATCATCTCTGGCTGTGTCTGCAGGAGGAAAG GTCACTATGAGCTGTAAGTCCAGTCAAAGTGTTTTATACAGTTCAAATCAGAAGA ACTACTTGGCCTGGTACCAGCAGAAACCAGGGCAGTCTCCTAAACTACTGATCTA CTGGGCATCCACTAGGGAATCTGGTGTCCCTGATCGCTTCACAGGCAGTGGATCT GGGACAGATTTTACTCTTACCATCAGCAGTGTACAAGCTGAAGACCTGGCAGTTT ATTACTGTCATCAATACCTCTCCTCGTGGACGTTCGGTGGAGGCACCAAGCTGGA AATCAAA |
| 11 | | VH1 | GAAGTGATGCTGGTGGAGTCTGGGGGAGGCTTAGTGAAGCCTGGAGGGTCCCT CCAACTCTCCTGTGCAGCCTCTGGATTCACGTTCAGTGACTATGCCATGTCTTGGG TTCGCCAGACTGCGGAGACGAGGCTGGAGTGGGTCGCAACCATCAGTGATGGT GGTAGTCACACCTACTATCCAGACAGTGTGAGGGGACGGTTCACCATCTCCAGA GACAATGCCAAGAAGGCCCTGTACCTGGAAATGAGCAGTCTGAAGTCTGAGGAC ACGGCCATGTATTACTGTGGAAGACGGGCGGGGAGGTACGATGAGAGAGATGC TATGGACTACTGGGGTCAAGGAACCACAGTCACCGTCTCCTCA |
| 12 | | VH2 | TCTGATGTACAGCTTCAGGAGTCAGGACCTGGCCTCGTGAAACCTTCTCAGTCTCT GTCTCTCACCTGCTCTGTCACTGGCTACTCCATCACCAGTGGTTTTTACTTAAACT GGATCCGGCAGTTTCCAGGAAACAAACTGGAATGGATGGGCTACATAAACTACG GTGGTAGCATTAACTACAACCCATCTCTCAAAAGTCGCATCTCCATCACTCGTGAC ACATCTAAGAACCAGTTTTTCCTGAGGTTGAATTCTGTGACTGCTGAGGACACAG CCACATATTACTGTGCAACCATGCCTAACTCCTGGTACTTCGATGTCTGGGGCAC AGGGACCACGGTCACCGTCTCCTCA |

TABLE 3 -continued

Nucleic acid sequences encoding for the variable light chain or variable heavy chains of antibodies EV18, 19 and 20.

| SEQ ID No. | Hybridoma | Chain | Sequences |
|---|---|---|---|
| 13 | E20/5 | VL | AGTATTGTGATGACCCAGACTCCCAAATTCCTGCCTGTATCAGCAGGAGACAGG<br>GTTACCATGACCTGCAAGGCCAGTCAGAGTGTGGGTAATAATGTAGCCTGGTAC<br>CAACAGAAGTCAGGACAGTCTCCTAAACTGCTGATATACTATGCATCCAATCGCT<br>ACACTGGAGTCCCTGATCGCTTCACTGGCAGTGGATCTGGGACAGATTTCACTTT<br>CACCATCAGCAGTGTGCAGGTTGAAGACCTGGCAGTTTATTTCTGTCAGCAGCAT<br>TATAGCTCTCCTCCCACGTTCGGTGCTGGGACCAAGCTGGAGCTGAAA |
| 14 | | VH | GAAGTGCAGCTGGTGGAGTCTGGGGGAGGCTTAGTGAAGCCTGGAGGGTCCCT<br>GAAACTCTCCTGTGCAGCCTCTGGATTCACTTTCAACATCTATGCCATGTCTTGGG<br>TTCGCCAGACTCCGGAAAAGAGGCTGGAGTGGGTCGCAACCATTAGTGATGGTG<br>GTAGTTATACCTACTATCCAGACAATGTAAAGGGCCGATTCACCATCTCCAGAGA<br>CAATGCCAAGAACAACCTGTACCTGCAAATGAGCCATCTGAAGTCTGAGGACAC<br>AGCCATGTATTACTGTGTAAGAGATCGAGGAAATTACTACAGTAGAGCGTTCCC<br>GTATGCTTACTGGGGCCAAGGGACTCTGGTCACTGTCTCTGCA |

In particular, the isolated nucleic acid molecule may comprise at least one nucleic acid sequence having at least 80%, at least 90%, or at least 95% sequence identity to SEQ ID NOs: 8, 10, or 13, and/or at least one nucleic acid sequence having at least 80%, at least 90%, or at least 95% sequence identity to SEQ ID NOs: 9, 11, 12, or 14 as listed in Table 3.

The isolated nucleic acid molecule according to the invention may be cloned into an expression vector, which may in turn be transformed into a host cell for the production of an antibody according to any aspect of the present invention. In particular, the host cell may be 293 cells, CHO cells or recombinant plant cells.

Techniques developed for the production of "chimeric antibodies" (Morrison, et al., 1984 incorporated herein by reference in their entirety) by splicing the genes from a mouse antibody molecule of appropriate antigen specificity together with genes from a human antibody molecule of appropriate biological activity can be used. For example, the genes from a mouse antibody molecule such as E18, E19, and E20 can be spliced together with genes from a human antibody molecule of appropriate biological activity. A chimeric antibody is a molecule in which different portions are derived from different animal species, such as those having a variable region derived from a murine antibody and a human immunoglobulin constant region. Chimeric antibodies are also those that contain a human Fc portion and a murine (or other non-human) Fv portion.

Techniques have been developed for the production of humanized antibodies (e.g., U.S. Pat. Nos. 5,585,089 and/or 5,225,539, which are incorporated herein by reference in their entirety). An immunoglobulin light or heavy chain variable region consists of a "framework" region interrupted by three hypervariable regions, referred to as complementarity determining regions (CDRs). Briefly, humanized antibodies are antibody molecules from non-human species having one or more CDRs from the non-human species and a framework region from a human immunoglobulin molecule. Both chimeric and humanized antibodies may be monoclonal. Such human or humanized chimeric antibodies may be preferred for use in in vivo diagnosis or therapy of human diseases or disorders.

Recombinant chimeric E18 (VL+VH; SEQ ID NOs: 1 and 2), recombinant chimeric E19 (VL+VH & VL+VH2; SEQ ID NOs: 3, 4 and 5) and recombinant chimeric E20 (VL+VH; SEQ ID NOs: 6 and 7) antibodies were generated. For E18, a second recombinant chimeric antibody was made by altering E18 VL (SEQ ID NO: 1) and the new VL sequence (SEQ ID NO: 15, VL2) is shown in Table 4. Additionally, seven recombinant humanized E19 VL and VH sequences, derived from E19 VL and VH2 (SEQ ID NOs: 3 and 5), were generated. The seven new recombinant humanized E19 VL and VH amino acid sequences are shown in Table 4 as hVL or hVH chains (SEQ ID NOs: 16, 17, 18, 19, 20, 21 and 22; hVL1, hVL2, hVL3, hVH1, hVH2, hVH3, hVH4, respectively).

TABLE 4

Polypeptide sequences encoding for variable light chains or variable chains heavy of additional chimeric and humanized recombinant E18 and E19 antibodies.

| SEQ ID NO. | Recombinant | Chain | Sequences |
|---|---|---|---|
| 15 | derived from E18 VL (SEQ ID NO. 1) | VL2 | DIKMTQSPSSMYASLGERVTITCKASQDIKSYLSWYQQKPWKSPKTLIYYAKNL<br>ADGVPSRFSGSGFGQDYSLTISSLESDDTATYYCLQHGESPYTFGSGTKLEIK |
| 16 | derived from E19 VL (SEQ ID NO. 3) | hVL1 | NIMMTQSPDSLAVSLGERATINCKSSQSVLYSSNQKNYLAWYQQKPGQPPKLLIY<br>WASTRESGVPDRFSGSGSGTDFTLTISSLQAEDVAVYYCHQYLSSWTFGQGTKVE<br>IK |
| 17 | derived from E19 VL (SEQ ID NO. 3) | hVL2 | NIMMTQSPDSLAVSLGERATINCKSSQSVLYSSNQKNYLAWYQQKPGQSPKLLIY<br>WASTRESGVPDRFSGSGSGTDFTLTISSLQAEDVAVYYCHQYLSSWTFGGGTKVE<br>IK |

TABLE 4 -continued

Polypeptide sequences encoding for variable light chains or variable chains heavy of additional chimeric and humanized recombinant E18 and E19 antibodies.

| SEQ ID NO. | Recombinant | Chain | Sequences |
|---|---|---|---|
| 18 | derived from E19 VL (SEQ ID NO. 3) | hVL3 | NIMMTQSPDSLALSLGERATINCKSSQSVLYSSNQKNYLAWYQQKPGQSPKLLIY WASSRESGVPDRFSGSGSGTDFTLTISSLQAEDVALYYCHQYLSSWTFGGGTKVE IK |
| 19 | derived from E19 VH2 (SEQ ID NO. 5) | hVH1 | DVQLQESGPGLVKPSQTLSLTCTVSGYSITSGFYLNWIRQHPCKGLEWIGYINYG GSINYNPSLKSRVTISRDTSKNQFSLKLSSVTAADTAVYYCATMPNSWYFDVWGR GTLVTVSS |
| 20 | derived from E19 VH2 (SEQ ID NO. 5) | hVH2 | DVQLQESGPGLVKPSQTLSLTCTVSGYSITSGFYLNWIRQHPGKKLEWIGYINYG GSINYNPSLKSRVTISRDTSKNQFSLKLSSVTAADTAVYYCATMPNSWYFDVWGT GTLVTVSS |
| 21 | derived from E19 VH2 (SEQ ID NO. 5) | hVH3 | EVQLVESGPGLVKPSQTLSLTCTVSGYSITSGFYLNWVRQHPGKKLEWIGYINYG GSINYNPSLKSRVSISRDTSKNQFSLKLTSVTAADTAVYYCATMPNSWYFDVWGT GTLVTVSS |
| 22 | derived from E19 hVH2 (SEQ ID NO. 20) | hVH4 | DVQLQESGPGLVKPSQTLSLTCTVSGYSITSGFYLNWIRQHPGKKLEWIGYINYG GSINYNPSLKSRVTISRDTSKNQFSLKLSSVTAADTAVYYCARTMPNSWYFDVWG TGTLVTVSS |

According to another preferred aspect of the present invention, there is provided an isolated nucleic acid molecule encoding at least one variable light chain of an antibody according to any aspect of the present invention, or a variant, mutant or fragment thereof, and at least one variable heavy chain of an antibody according to any aspect of the present invention, or a variant, mutant of fragment thereof. In particular the isolated nucleic acid molecule may encode at least one of SEQ ID NOs: 15, 16, 17 and 18, a variant, mutant or fragment thereof and at least one of SEQ ID NOs: 19, 20, 21 and 22, a variant, mutant or fragment thereof. The nucleic acid sequences encoding the respective variable light chains or variable heavy chains of chimeric and humanized recombinant E18 and E19 antibodies are listed in Table 5.

TABLE 5

Nucleic acid sequences encoding for variable light chains or variable heavy chains of chimeric and humanized recombinant E18 and E19 antibodies.

| SEQ ID NO. | Recombinant | Chain | Sequences |
|---|---|---|---|
| 23 | derived from E18 VL (SEQ ID NO. 1) | VL2 | GACATCAAGATGACCCAGTCTCCATCCTCCATGTATGCATCGCTGGGAGAGAGAGTC ACTATCACTTGCAAGGCGAGTCAGGACATTAAAAGCTATTTAAGCTGGTACCAGCA GAAACCATGGAAATCTCCTAAGACCCTGATCTATTATGCAAAAAACTTGGCAGATGG GGTCCCATCAAGATTCAGTGGCAGTGGATTTGGGCAAGATTATTCTCTAACCATCAG CAGCCTGGAGTCTGACGATACAGCAACTTATTACTGTCTACAGCATGGTGAGAGCCC GTATACGTTCGGATCGGGGACCAAACTGGAAATAAAA |
| 24 | derived from E19 VL (SEQ ID NO. 3) | hVL1 | AATATCATGATGACCCAGTCCCCCGACTCCCTGGCCGTGTCTCTGGGAGAGAGAGCC ACCATCAACTGCAAGTCCTCCCAGTCCGTGCTGTACTCCTCCAACCAGAAGAACTAC CTGGCCTGGTATCAGCAGAAGCCCGGCCAGCCTCCCAAGCTGCTGATCTACTGGGC CTCCACCCGGGAATCTGGCGTGCCCGATAGATTCTCCGGCTCCGGCTCTGGCACCGA CTTTACCCTGACCATCAGCTCCCTGCAGGCCGAGGATGTGGCCGTGTACTACTGCCA CCAGTACCTGTCCTCTTGGACCTTCGGCCAGGGCACCAAGGTGGAAATCAAG |
| 25 | derived from E19 VL (SEQ ID NO. 3) | hVL2 | AATATCATGATGACCCAGTCCCCCGACTCCCTGGCCGTGTCTCTGGGAGAGAGAGCC ACCATCAACTGCAAGTCCTCCCAGTCCGTGCTGTACTCCTCCAACCAGAAGAACTAC CTGGCCTGGTATCAGCAGAAGCCCGGCCAGTCCCCTAAGCTGCTGATCTACTGGGC CTCCACCCGGGAATCTGGCGTGCCCGATAGATTCTCCGGCTCCGGCTCTGGCACCGA CTTTACCCTGACCATCAGCTCCCTGCAGGCCGAGGATGTGGCCGTGTACTACTGCCA CCAGTACCTGTCCTCTTGGACCTTCGGCGGAGGCACCAAGGTGGAAATCAAG |
| 26 | derived from E19 VL (SEQ ID NO. 3) | hVL3 | AATATCATGATGACCCAGTCCCCCGACTCCCTGGCCCTGTCTCTGGGAGAGAGAGCC ACCATCAACTGCAAGTCCTCCCAGTCCGTGCTGTACTCCTCCAACCAGAAGAACTAC CTGGCCTGGTATCAGCAGAAGCCCGGCCAGTCCCCTAAGCTGCTGATCTACTGGGC CTCCTCCCGGGAATCTGGCGTGCCCGATAGATTCTCCGGCTCCGGCTCTGGCACCGA CTTTACCCTGACCATCAGCTCCCTGCAGGCCGAGGATGTGGCCCTGTACTACTGCCA CCAGTACCTGTCCTCTTGGACCTTCGGCGGAGGCACCAAGGTGGAAATCAAG |

TABLE 5 -continued

Nucleic acid sequences encoding for variable light chains or variable heavy chains of chimeric and humanized recombinant E18 and E19 antibodies.

| SEQ ID NO. | Recombinant | Chain | Sequences |
|---|---|---|---|
| 27 | derived from E19 VH2 (SEQ ID NO. 5) | hVH1 | GATGTGCAGCTGCAGGAATCTGGCCCTGGCCTCGTGAAGCCTTCCCAGACCCTGTCT CTGACCTGCACCGTGTCCGGCTACTCCATCACCTCCGGCTTCTACCTGAACTGGATCC GGCAGCACCCCTGCAAGGGCCTGGAATGGATCGGCTACATCAACTACGGCGGCTCT ATCAACTACAACCCCAGCCTGAAGTCCAGAGTGACCATCTCCCGGGACACCTCCAAG AACCAGTTCTCCCTGAAGCTGTCCTCCGTGACCGCCGCTGATACCGCCGTGTACTAC TGCGCTACCATGCCCAACAGCTGGTACTTCGACGTGTGGGGCAGAGGCACCCTCGT GACCGTGTCATCT |
| 28 | derived from E19 VH2 (SEQ ID NO. 5) | hVH2 | GATGTGCAGCTGCAGGAATCTGGCCCTGGCCTCGTGAAGCCTTCCCAGACCCTGTCT CTGACCTGCACCGTGTCCGGCTACTCCATCACCTCCGGCTTCTACCTGAACTGGATCC GGCAGCACCCCGGCAAGAAACTGGAATGGATCGGCTACATCAACTACGGCGGCTCT ATCAACTACAACCCCAGCCTGAAGTCCAGAGTGACCATCTCCCGGGACACCTCCAAG AACCAGTTCTCCCTGAAGCTGTCCTCCGTGACCGCCGCTGATACCGCCGTGTACTAC TGCGCTACCATGCCCAACAGCTGGTACTTCGACGTGTGGGGCACCGGCACCCTCGT GACAGTGTCATCT |
| 29 | derived from E19 VH2 (SEQ ID NO. 5) | hVH3 | GAAGTGCAGCTGGTGGAATCTGGCCCTGGCCTCGTGAAGCCTTCCCAGACCCTGTCT CTGACCTGCACCGTGTCCGGCTACTCCATCACCTCCGGCTTCTACCTGAACTGGGTG CGACAGCACCCCGGCAAGAAACTGGAATGGATCGGCTACATCAACTACGGCGGCTC TATCAACTACAACCCCAGCCTGAAGTCCCGGGTGTCCATCTCCCGGACACCTCCAA GAACCAGTTCTCCCTGAAGCTGACCTCCGTGACCGCCGCTGATACCGCCGTGTACTA CTGCGCTACCATGCCCAACAGCTGGTACTTCGACGTGTGGGGCACCGGCACCCTCGT GACAGTGTCATCT |
| 30 | derived from E19 hVH2 (SEQ ID NO. 20) | hVH4 | GATGTGCAGCTGCAGGAATCTGGCCCTGGCCTCGTGAAGCCTTCCCAGACCCTGTCT CTGACCTGCACCGTGTCCGGCTACTCCATCACCTCCGGCTTCTACCTGAACTGGATCC GGCAGCACCCCGGCAAGAAACTGGAATGGATCGGCTACATCAACTACGGCGGCTCT ATCAACTACAACCCCAGCCTGAAGTCCAGAGTGACCATCTCCCGGGACACCTCCAAG AACCAGTTCTCCCTGAAGCTGTCCTCCGTGACCGCCGCTGATACCGCCGTGTACTAC TGCGCTCGCACCATGCCCAACAGCTGGTACTTCGACGTGTGGGGCACCGGCACCCT CGTGACAGTGTCATCT |

In particular, the isolated nucleic acid molecule may comprise at least one sequence having at least 80%, at least 90%, or at least 95% sequence identity to SEQ ID NOs: 23, 24, 25 or 26, and at least one sequence having at least 80%, at least 90%, or at least 95% sequence identity to SEQ ID NOs: 27, 28, 29 or 30 listed in Table 5.

The isolated nucleic acid molecule according to a preferred aspect of the invention may be cloned into an expression vector, which may in turn be transformed into a host cell for the production of an antibody according to any aspect of the present invention. In particular, the host cell may be 293 cells, CHO cells or recombinant plant cells. The recombinant chimeric and humanized E18, E19 and E20 antibodies provide an additional extremely stable continuous source of the antibodies and the binding proteins of the invention.

Antibody fragments that contain the idiotype of the antibody molecule can be generated by known techniques. For example, such can be produced by pepsin digestion of the antibody molecule; the Fab fragments can be generated by reducing the disulfide bridges of the F(ab)2 fragment, and the Fab fragments which can be generated by treating the antibody molecule with papain and a reducing agent. Such antibody fragments can be generated from any of the antibodies of the invention.

In the production of antibodies, screening for the desired antibody can be accomplished by techniques known in the art. For example, these techniques may include but are not limited to radioimmunoassay, enzyme-linked immunosorbent assay (ELISA), "sandwich" immunoassays, immunoradiometric assays, gel diffusion precipitin reactions, immunodiffusion assays, in situ immunoassays (using colloidal gold, enzyme, radioisotope labels or the like), western blots, precipitation reactions, agglutination assays (gel agglutination assays, hemagglutination assays or the like), immunofluorescence assays, immunoelectrophoresis assays and the like. For example, the antibody binding may be detected by detecting a label on the primary antibody. In another example, the primary antibody may be detected by detecting binding of a secondary antibody or other reagent to the primary antibody. The secondary antibody may be labeled.

According to other preferred aspects of the present invention, there is provided a method for characterizing at least one conformational neutralizing epitope on a potential *enterovirus* vaccine candidate, and a method for purifying a potential *enterovirus* vaccine candidate that contains at least one conformational epitope. Further, the present invention provides a method to define the neutralizing antibody potency for EV71.

According to an aspect of the invention, there is provided an isolated antibody or fragment thereof according to any aspect of the invention for use in medicine. In particular, the use relates to treating EV71-infection and/or at least one EV71-linked disease.

According to another aspect, the present invention provides a pharmaceutical composition comprising the isolated antibody or fragment thereof according to any aspect of the invention.

According to yet another aspect of the present invention there is provided at least one method of treating EV71-infection and/or at least one EV71-linked disease, the method comprising administering to a subject an isolated antibody according to any aspect of the invention. In a preferred embodiment, a combination or mixture of antibodies of the invention may be administered to the subject. For example, the combination or mixture may comprise humanized or chimeric E19 as hereinbefore described and at least one additional antibody selected from humanized or chimeric E18 or humanized or chimeric E20 as hereinbefore described. Preferably, the combination or mixture comprises humanized E19 as hereinbefore described and humanized or chimeric E18. In particular, the EV71-linked disease may be selected from the group consisting of aseptic meningitis, encephalitis, cranial nerve palsies, Guillan-Barre syndrome, brainstem encephalitis, poliomyelitis-like syndrome, herpangina, and Hand, Foot and Mouth disease.

According to yet another aspect of the present invention there is provided a use of at least one antibody according to any aspect of the invention for the preparation of a medicament for treating EV71-infection and/or at least one EV71-linked disease. In a preferred embodiment, the medicament may comprise humanized or chimeric E19 as hereinbefore described and at least one additional antibody selected from humanized or chimeric E18 or humanized or chimeric E20 as hereinbefore described. Preferably, the medicament comprises humanized E19 as hereinbefore described and humanized or chimeric E18. In particular, the EV71-linked disease may be selected from the group consisting of aseptic meningitis, encephalitis, cranial nerve palsies, Guillan-Barre syndrome, poliomyelitis-like syndrome, brainstem encephalitis, herpangina, and Hand, Foot and Mouth disease.

Having now generally described the invention, the same will be more readily understood through reference to the following examples which are provided by way of illustration, and are not intended to be limiting of the present invention.

A person skilled in the art will appreciate that the present invention may be practised without undue experimentation according to the method given herein. The methods, techniques and chemicals are as described in the references given or from protocols in standard biotechnology and molecular biology text books.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1

Production of Hybridoma Cell Lines Against EV71

Ten 8-week old Balb/c mice were immunized with recombinant EV71-VP0 protein with the SUMO fusion protein cleaved off. The first immunization was done in Freund's Complete Adjuvant (Santa Cruz, Calif., United States) and was injected subcutaneously (SC). The second, third, and pre-fusion booster doses were in Freund's Incomplete Adjuvant (Santa Cruz, Calif., United States) and were done 2-3 weeks apart by intraperitoneal injection (IP).

Three days after the pre-fusion priming injections, the mice spleens were ready for cell fusion (Appendix B: Protocol for Spleen-Myeloma Cell Fusion). Prior to cell fusion, the partner SP2/0 myeloma cell line was expanded to one T75 flask per spleen. On the day of the cell fusion, the mice were bled from the heart to collect sera and the spleens were harvested in an aseptic manner. Both the spleen cells and the SP2/0 cells were washed and mixed at a ratio of one mouse spleen to one T75 flask of SP2/0 cells. The mice spleens were divided into four cell fusion groups according to immunogens, and the appropriate number of SP2/0 cells were added. The cell fusions were performed by slowly adding polyethylene glycol (PEG1500) (Sigma, Missouri, United States) to the cell mixture and the resulting cell pellet was washed, then plated into four 24-well tissue culture plates per spleen (Master Plates). After an overnight incubation, 10% RPMI 2XHAT medium (hypoxanthine, aminopterin and thymidine) was added to the wells and the plates were incubated for several days before follow-up feeding with 10% RPMI 1XHAT.

One week to 10 days after the fusion, visible hybridoma clones were picked from the Master Plates into 24-well Picked Clone Plates. When these picked clones were 40-70% confluent, the cell supernatants were screened by Enzyme-Linked Immunosorbent Assay (ELISA) with plates coated with EV71 VLP Lysate (antigen) and Sf9 Lysate (control). A second screen was conducted by ELISA with plates coated with a cocktail of recombinant EV71 viral proteins (rVP0, rVP1, rVP2, rVP3, rVP4). Any samples that gave a positive reading (SN07>0.1 OD, Sf9<0.1) were amplified to T25 flasks and cryopreserved. Any potentially positive clones were then run on a Mouse Immunoglobulin Capture ELISA (MICE) to ensure the clones were secreting antibodies. Antibody-producing cell supernatants were collected from the samples and were used to test for neutralization of the EV71 virus.

The strongest positive hybridomas were then selected for recloning by a limiting dilution method to obtain single clones in the wells of 96-well plates (Appendix E: Recloning Monoclonal Antibody Cell Lines Protocol). Recloning is needed because the original cultures may have originated from more than one hybridoma cell. Through recloning, single cells from this antibody-positive culture can now be isolated and subcultured. The recloned cells were first screened by MICE for cells that secrete antibodies at a high titer (determined by OD measurements). 4-8 single clones with high OD readings were expanded into the wells of 24-well plates and were then tested for specific reactivity via indirect ELISA using plates coated with EV71 VLP Lysate/ Retentate. Clones that had strong specific reactivities were expanded to T25 flasks and cryopreserved. One good clone was chosen for another round of recloning. After two rounds of recloning, the final clones were expanded for the purposes of collecting cell supernatants to be used directly as reagents or for purification of monoclonal antibodies. The final clones were also isotyped through a pre-coated ELISA plate with different anti-mouse-Ig types (anti-IgG1, IgG2a, IgG2b, IgG3, IgA, IgM, Kappa and Lambda light chains) (Appendix C-III: Protocol for Pierce Rapid ELISA Mouse Monoclonal Isotyping Kit). In addition, RNA was isolated from each hybridoma and used to produce cDNA for sequencing of each variable light and variable heavy chain.

Preparation of Fab Fragments of Monoclonal Antibodies

The Fab fragments of the antibodies were prepared with the use of the Pierce Fab Preparation Kit according to the manufacturer's instructions having the website address world wide web dot piercenet dot com/product/fab-preparation-kits.html. Animal care and use was conducted in accordance with the National Animal Welfare Standards and Guidelines of Malaysia under the Animals Act of 2006.

Immunoblot Analysis

Equal volume of mock- and EV71-infected cell lysates were separated on a 12% SDS-PAGE, transferred to nitrocellulose membrane, and probed with R525 (polyclonal antibody against EV71 VP1), E18 or E19. Bound antibody was detected by incubation with horseradish peroxidase conjugated secondary antibodies (Dako, Denmark) followed by TMB membrane peroxidase substrate (KPL, Maryland, USA).

ELISA Analyses

An indirect ELISA was performed by coating Nunc Immuno plate with recombinant viral proteins or heat-inactivated EV71 infected RD cell lysates as positive control. Nonspecific binding was blocked using 5% skim milk, antibodies were added at various concentrations in duplicate, and bound antibodies were detected using horseradish peroxidase conjugated (HRP)-conjugated anti-mouse IgG (Dako). SureBlue Reserve TMB microwell peroxidase substrate (KPL) was added for 5 min, 0.5 M HCl was added to stop the enzyme reaction and wells were read at 450 nm.

A sandwich ELISA was performed where the wells were coated with R525 antibody against VP1, and PEG precipitated EV71 that was untreated or heat inactivated at 56° C. for 30 minutes was allowed to bind to the VP1 antibody. The bound particles were detected by the monoclonal antibodies E18 or E19, followed by HRP IgG (Dako) as described above.

A competitive ELISA was conducted to examine the presence of antibodies containing E18 epitope in mouse serum. Sera from four mice immunized with VLP that had high PRNT50 titres were pooled and sera from four mice immunized with PBS were pooled for the competitive ELISA assay. Wells were coated with R525 followed by equal protein concentrations of mock and EV71-infected RD cell lysates. Sera pooled from mice (at 1/250 dilution) were added into the wells and HRP-conjugated E18 was added immediately after. Reserve TMB microwell peroxidase substrate (KPL) was added for 5 min, 0.5 M HCl was added to stop the enzyme reaction and wells were read at 450 nm. Adjusted OD values were obtained by subtracting OD (mock RD cell lysate) from OD (EV71-infected RD cells). The relative percentage of binding of E18 was derived by dividing the adjusted OD of samples by the adjusted OD of well containing only HRP-E18, multiplied by 100.

Plaque Reduction Neutralization Test

Different concentrations of Antibodies, Fab fragments or heat-inactivated mouse serum were incubated in 1:1 volume ratios with infectious EV71 strain MY104 (300 PFU/mL) for 1 hour at 37° C. The virus-antibody (or Fab) mixture was inoculated in duplicates over Vero cell monolayers in 24 well plates (Nunc, Thermo-Fisher, USA). The monolayers were prepared with 0.5 ml per well of Vero cells at 3×105 per ml in DMEM supplemented with 5% FBS and antibiotics (all from Invitrogen, Carlsbad, Calif., USA) and left to adhere overnight before inoculation. Media was aspirated before inoculation with 200 µl of the antibody (or Fab)-virus mixtures and incubated in a $CO_2$ incubator at 37° C. for 2 hours before 1 ml of overlay was added containing DMEM supplemented with 2% FBS, antibiotics and 1.5% carboxymethyl cellulose (CMC). Plates were incubated at 37° C. with 5% $CO_2$ for 4 days and stained with naphthalene black. Plaques were counted manually. The percent inhibition was determined relative to controls in which the mean number of plaques in wells in which the virus had been incubated with media alone.

Virus Production and Purification

EV71 virions were produced and purified as described previously (4).

VLP Production and Purification

Briefly, EV71 empty immature capsids were produced using a baculovirus expression system where the complete P1 coding sequence and the protease 3CD of EV71 were recombinantly inserted downstream of the polyhedrin promoter and the recombinant baculovirus was used to infect Sf9 cells at an moi of 0.1. The supernatant harvested on day 4 was clarified and concentrated using tangential flow filtration (GE Healthcare Lifesciences) and the retentate was run through an affinity column prepared by coupling E18 to a HiTrap NHS-activated HP column (GE Healthcare Lifesciences). The particles bound were eluted using a glycine buffer at pH 3.0 and immediately neutralized to pH7.2 with 1M Tris-HCl. The particles were transferred to Dulbecco's Phosphate Buffered Saline (DPBS) buffer (Invitrogen).

Characterization of EV71 VLP by Pull-Down Assay 20 ml of supernatant from cells infected with recombinant baculovirus expressing EV71 VLPs was mixed with 10 ml neutralizing monoclonal antibody E18 and left at room temperature for 1 hr. The mixture was loaded slowly through a 1 ml column of MabSelect SuRe™ (GE Healthcare) recombinant Protein A, 85 um agarose bead size, which was pre-equilibrated with PBS, then washed with 20 mls PBS and then eluted with 0.5 ml of 0.1M glycine-HCl, pH3.0. Fractions were neutralized with 30 µl of Tris-HCl, pH8.8. Elution fractions were run on SDS-PAGE followed by Coomassie blue staining and destaining.

Analysis of Affinity Column (AFC) Purified EV71 VLP

An affinity column (AFC) was prepared with a neutralizing monoclonal antibody E18. The eluted fraction was analyzed by Western blotting. The eluted fraction was probed using an anti-VP 1 antibody, an anti-VP2 antibody, or an anti-VP0 monoclonal antibody.

E18-purified VLPs were analyzed using electron microscopy (EM).

Immunization of Mice

Mice (n=10 per group) were immunized with two doses of DPBS or 10 µg of VLP in the presence of Inject Alum (Thermo Scientific), 3 weeks apart. Serum were inactivated by incubation at 56° C. for 30 min, and stored at −20° C. for further analysis.

Recombinant Chimeric E18 and Humanized E19 Monoclonal Antibody Expression in Plant Cells The VL and VH DNA sequences (SEQ ID NOs: 23, 9, 25 and 30) were codon optimized for expression in *Nicotiana benthamiana* and genetically fused to a human IgG backbone that had also been codon optimized for expression in *Nicotiana benthamiana*. The chimeric E18 and fully humanized E19 antibody constructs were subsequently transferred into the agrobacteria and used to infiltrate wildtype *Nicotiana benthamiana* to produce recombinant plants. Recombinant chimeric E18 or fully humanized E19 antibody was harvested from plant material and purified using Protein A-based column chromatography. All methods used here were identical to those used previously for human therapeutic antibodies (Qiu et al., 2014).

Results

Figure 1B:
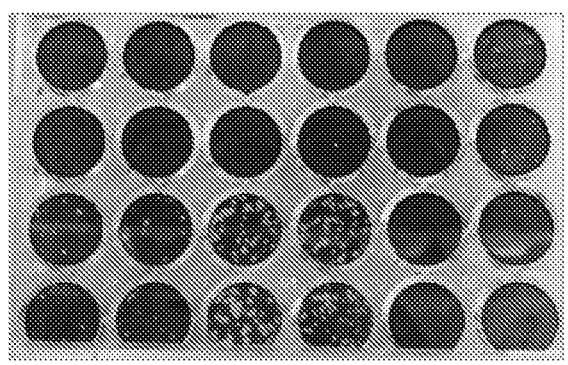
Figure 1C:
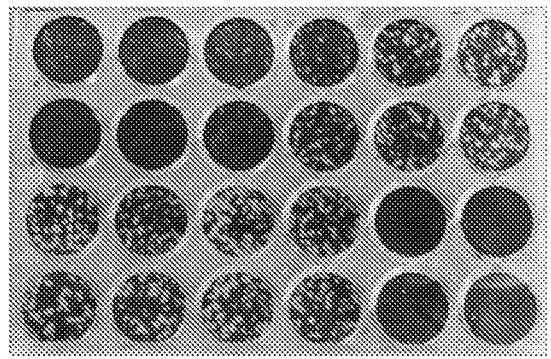

The antibodies, E18, E19, and E20 were prepared by immunizing mice with empty, immature EV71 particles containing VP0. Results from the plaque reduction neutralization test indicate that all three antibodies, E18, E19, and E20, are capable of neutralizing EV71 (FIGS. 1A-C). The $PRNT_{50}$ value for each antibody, which indicates the concentration of hybridoma culture fluid needed to reduce the number of plaques by 50% compared to the hybridoma-free virus is provided in Table 6.

TABLE 6

PRNT50 values for E18, E19, and E20.

| Antibody | PRNT$_{50}$ of original hybridoma |
|---|---|
| E18 | 0.625 µl/ml |
| E19 | 0.156 µl/ml |
| E20 | 5.0 µl/ml |

Figure 2:
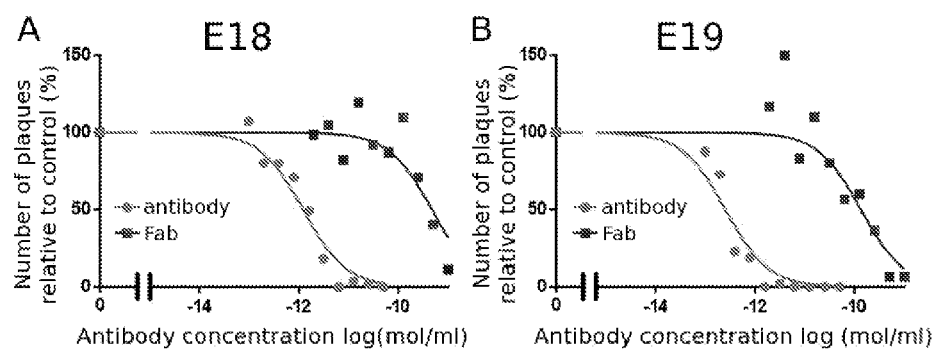
FIG. 2A is a graph showing the neutralization of EV71 by E18.
FIG. 2B is a graph showing the neutralization of EV71 by E19.

Further, both E18 and E19 could neutralize the virus as intact antibodies or as Fab fragments (FIG. 2). In FIG. 2, whole IgG and Fab fragments of the monoclonal antibodies E18 (panel a) and E19 (panel a) were used to inhibit EV71 at different concentrations (X axis) using a plaque reduction neutralization test. The circles represent whole antibody and the squares represent Fab fragments. Inhibition of virus was represented as the percentage of plaques relative to plaques in the control wells.

Figure 3:
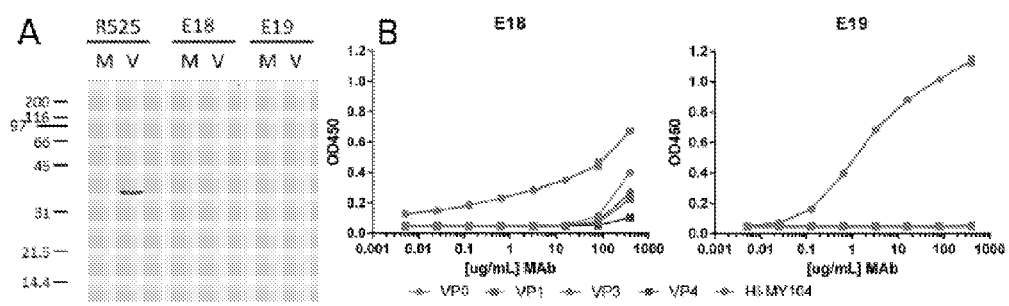
FIG. 3A is a Western blot image showing that E18 and E19 do not bind to denatured EV71 viral proteins. R525 is a rabbit polyclonal antibody against VP1; M=mock infected cell lysate; V=EV71 infected cell lysate.
FIG. 3B are binding curves showing binding of E18 and E19 to the recombinant and heat-inactivated EV71 capsid proteins.
Figure 4:
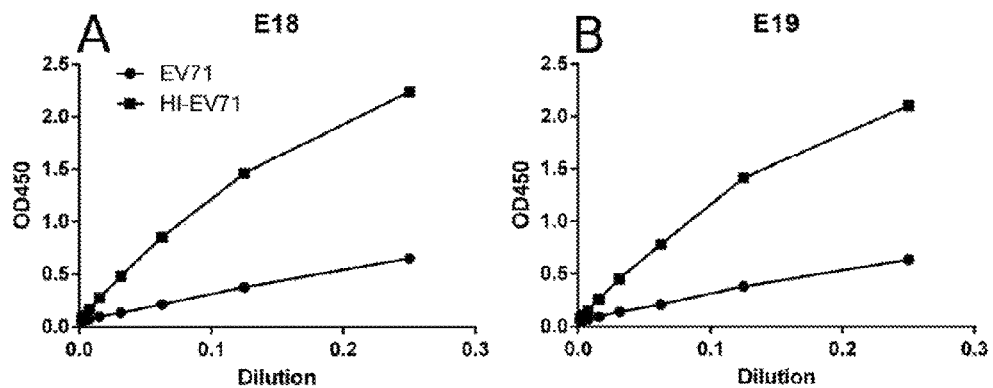
FIGS. 4A and B are graphs showing binding of EV71 and heat-inactivated (Hl)-EV71 by (A) E18 and (B) E19.

Results from indirect ELISA also indicate that both E18 and E19 MAbs can recognize conformational epitopes on the surface of heat-inactivated EV71 particles (FIG. 3). In FIG. 3A, Mock—(M) and EV71-infected (V) cell lysates were separated by SDS-PAGE and transferred onto membrane. Membrane was probed with R525, E18 or E19. E18 and E19 did not bind denatured viral proteins. Referring to FIG. 3B, indirect ELISA was performed by coating wells with recombinant viral proteins or heat-inactivated EV71-infected cell lysates. Various concentrations of MAb were added in duplicates. The MAbs were detected by Horeseradish Peroxidase (HRP) assay. The amount of bound MAbs are presented as average OD450±standard deviations. ELISA tests further showed that E18 binds better to heat-induced EV71 A particles than to mature virions (FIG. 4).

Figure 5:
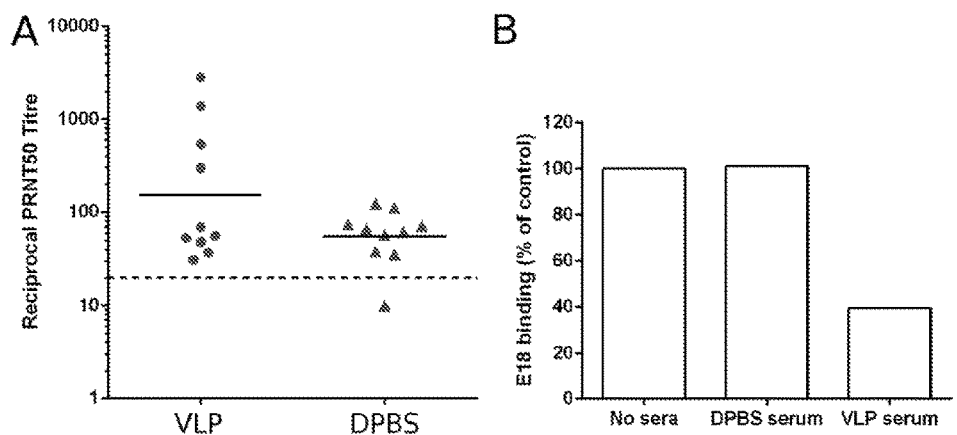
FIG. 5A is a dotted chart showing binding of antibodies in the sera of mice immunized with the Virus Like Particle (VLP) to EV71. DPBS is Dulbecco's Phosphate Buffered Saline.
FIG. 5B is a bar chart showing inhibition of E18 binding to EV71 in the presence of the sera of mice immunized with the VLP.

It has been shown here that antibodies capable of neutralizaing EV71 can be generated by immunization with immature picornavirus particles containing VP0. As an example of this strategy, empty immature virus like particles (VLPs) were purified on an E18 affinity column and were used to immunize mice. The resultant sera were assayed to determine the neutralizing antibody titres (FIG. 5). Mice immunized with VLPs exhibited higher neutralizing antibody titres against EV71 (geometric mean titre=153) compared to control mice (geometric mean titre=55). Pooled serum from VLP-immunized mice inhibited 60% of E18 binding indicating that serum from these mice contains antibodies that recognize E18 epitope (FIG. 5). Thus, VLPs selected for having the E18 epitope can induce neutralizing antibodies in mice. Therefore, therapeutic antibodies might also be obtainable for other picornaviruses using the approach described here.

Figure 6:
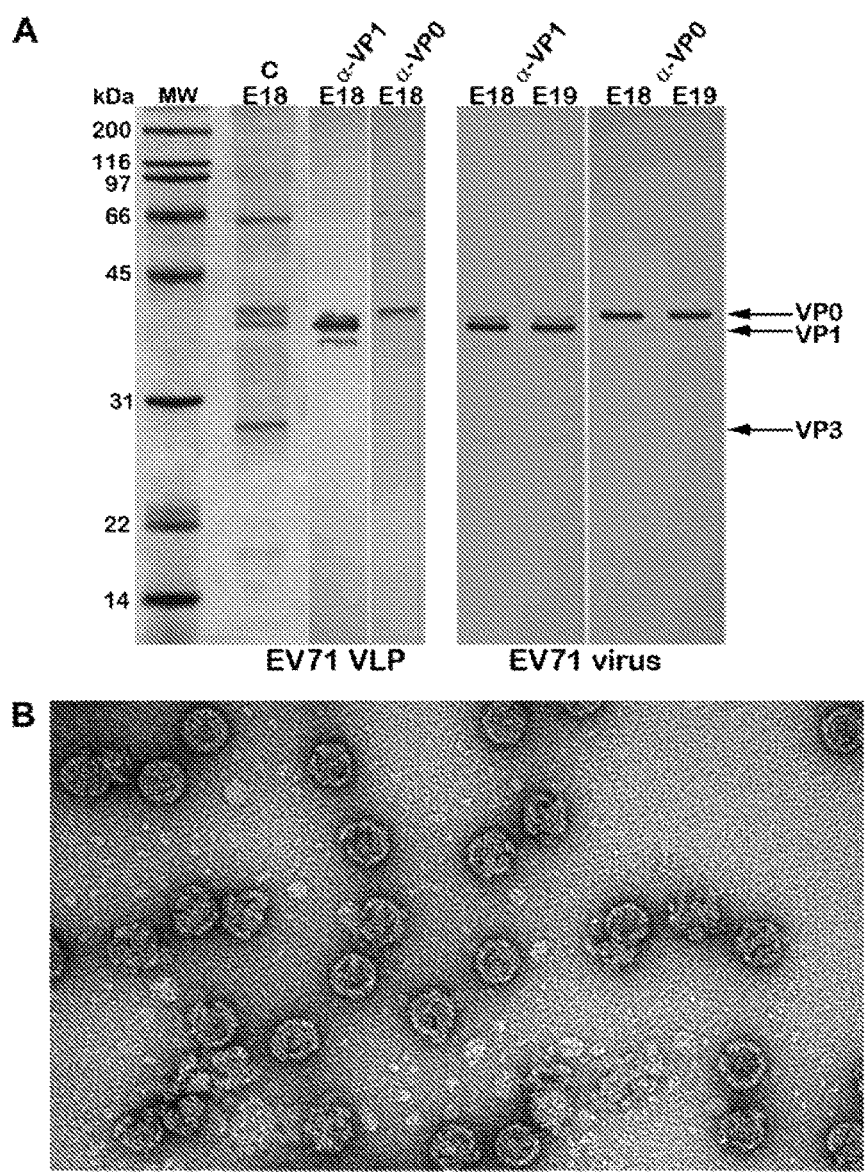
FIG. 6A is an image of a Coomassie-stained ("C") gel showing that antibody E18 can be used effectively to characterize potential EV71 vaccine candidates.
FIG. 6B is an image of EV71 virus like particles captured by antibody E18 affinity column.

Further, as E18 is capable of purifying immunogenic EV71 VLPs that maintain conformational epitopes it has utility as a process control reagent for EV71 vaccine development. An example of this process is presented in FIG. 6. Here, EV71 VLPs were able to bind to E18. As shown in FIG. 6A, the precipitated VLPs contained all of the individual VLP components (VP0, VP1 and VP3) when analyzed by SDS PAGE and stained with Coomassie Blue (labeled C). Next EV71 VLP purification was done using an E18 affinity column and eluted fractions were analyzed using Western blot. As shown in FIG. 6A the presence of VP1 and VP0 (next 2 lanes, labeled EV71 VLPs) in the purified VLPs was apparent. Importantly, affinity columns prepared with E18 as well as E19 both were used to purify infectious virions from native EV71 infected cultures and we could show the presence of VP1 and VP0 as shown in FIG. 6A (last 4 lanes labeled EV71 virus). Finally, E18, E19 and E20-purified VLPs were analyzed using electron microscopy (EM). In a representative example, VLPs approximately the same size as EV71 virions are shown in FIG. 6B. This demonstrates that the antibodies E18, E19 and E20 recognize a highly native assembled EV71 VLP as well as native infectious EV71 virions. Any EV71 vaccine candidate could be characterized similarly to determine if all components were present, that highly native conformational epitopes were present and/or if a structure resembling EV71 virions was evident. Further, as E18, E19 and E20 are highly neutralizing antibodies (FIG. 2, Table 6), the three antibodies could be used as standards for determining relative neutralization titers in individuals receiving candidate EV71 vaccines, providing a consistent standard for evaluating EV71 vaccine-induced antibody responses.

Figure 7:
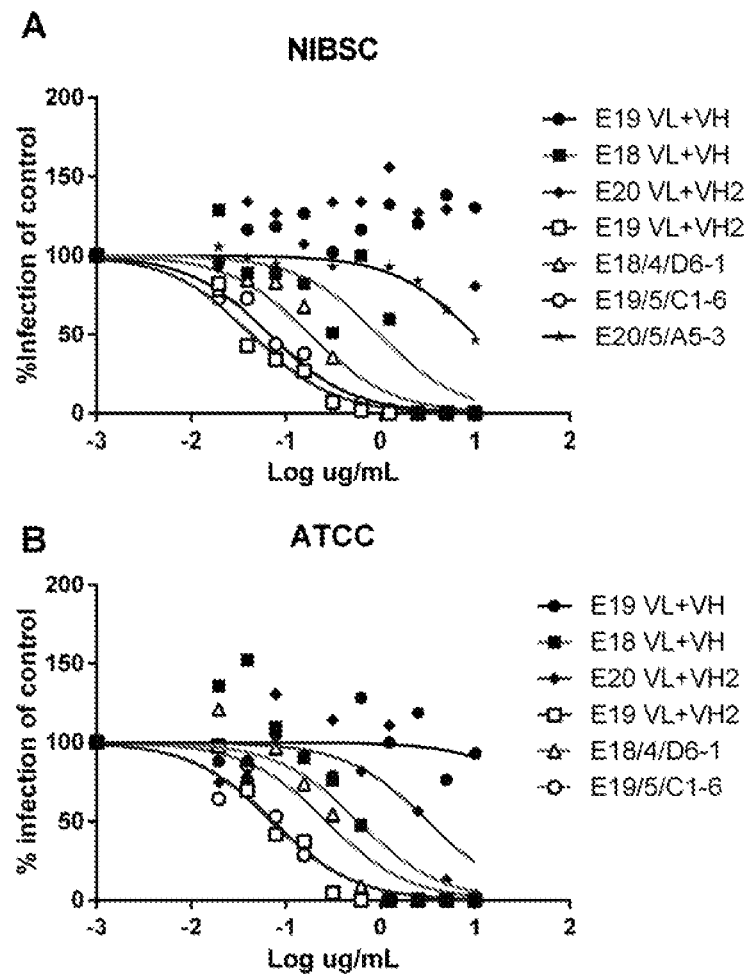
FIG. 7 includes two graphs showing the neutralization of EV71 by recombinant chimeric E18, E19 and E20 antibodies.

Importantly, the high neutralizing activity of E18, E19 and E20 also suggest these antibodies could be developed into effective therapeutic antibodies to treat human disease. As described above, both antibodies were originally purified from mouse hybridomas. As a first step towards developing E18, E19 and E20 as therapeutics for humans, recombinant chimeric E18, E19 and E20 antibodies were produced. Specifically the variable heavy and light chains of E18, E19 and E20 (SEQ ID NOs: 1, 2, 3, 4, 5, 6 and 7) were cloned into a human IgG backbone giving rise to recombinant mouse-human chimeric monoclonal antibodies. The chimeric antibodies were tested for their ability to neutralize EV71 in vitro and, as shown in FIG. 7, three of four recombinant chimeric antibodies neutralized virus. The E19 chimeric antibody that contained E19 VL+VH (SEQ ID NOs: 3 and 4) had no activity. Notably, chimeric E20 also showed weak neutralization with only limited activity present in one cell line (ATCC). Chimeric E18 showed significant neutralization activity; however, in both cell lines (NIBSC and ATCC) chimeric E18 activity was slightly less than the parental mouse antibody (EV18/4/D6-1). For chimeric E19 containing VL+VH2 (SEQ ID NOs: 3 and 5), neutralizing activity was greater than or equal to the parental mouse antibody (EV19/5/C1-6) in both cell lines. The concentration of recombinant chimeric antibody needed to inhibit 50% of EV71 growth, inhibitory concentration 50 (IC50) was extrapolated for each antibody and results are shown in Table 7.

TABLE 7

Recombinant chimeric E18, E19 and E20 antibody neutralization profiles

| Antibody | SEQ ID NOs | end point PRNT50 (ng/mL) | | Inhibitory concentration 50 (IC50) (ng/mL) | |
|---|---|---|---|---|---|
| | | Vero NIBSC | Vero ATCC | Vero NIBSC | Vero ATCC |
| Hybridoma EV18/4/D6-1 | | 312.5 | 625 | 180.6 | 272.1 |
| Recombinant chimeric E18 VL + VH | 1, 2 | 2500 | 625 | 965.9 | 585.1 |

TABLE 7-continued

Recombinant chimeric E18, E19 and E20 antibody neutralization profiles

| Antibody | SEQ ID NOs | end point PRNT50 (ng/mL) | | Inhibitory concentration 50 (IC50) (ng/mL) | |
|---|---|---|---|---|---|
| | | Vero NIBSC | Vero ATCC | Vero NIBSC | Vero ATCC |
| Hybridoma EV19/5/C1-6 | | 78.125 | 156.25 | 67.81 | 70.7 |
| Recombinant chimeric E19 VL + VH | 3, 4 | >10,000 | >10,000 | N/A | >10,000 |
| Recombinant chimeric E19 VL + VH2 | 3, 5 | 39.0625 | 78.125 | 43.22 | 73.51 |
| Hybridoma EV20/5/A5-3 | | 10,000 | N/A | 9952 | not tested |
| Recombinant chimeric E20 VL + VH | 6, 7 | >10,000 | 5,000 | N/A | 3179 |

The chimeric E19 antibody that contained E19 VL+VH (SEQ ID NO: 4) did not neutralize EV71 at any of the concentrations tested and chimeric E20 had the least neutralizing activity as demonstrated by the highest IC50. Recombinant chimeric E18 had a significantly higher IC50 in NIBSC cells than the parental mouse antibody (~5-fold difference) and the reduced neutralization was also evident in ATCC cells where the IC50 of chimeric E18 was ~2 fold higher than the parental antibody. Recombinant chimeric E19 containing VL+VH2 (SEQ ID NOs: 3 and 5) had the best activity as reflected by the low IC50 in both cell lines.

Figure 8:
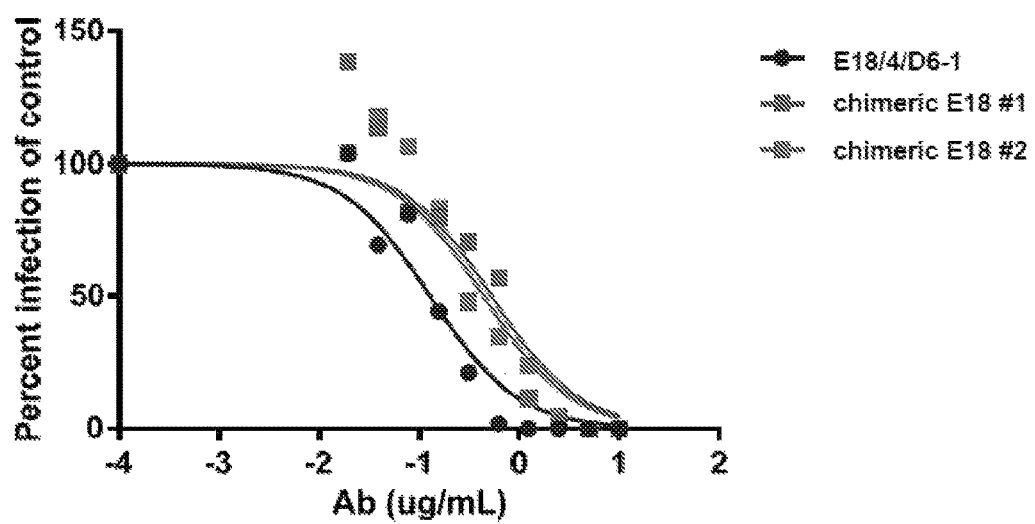
FIG. 8 shows EV71 neutralizing activity of the parental mouse E18 and chimeric E18 antibodies in cell culture using Vero cells. Y-axis=percentage plaque reduction; X-axis=log 10 scale of antibody concentration. Plant and non-plant-produced chimeric E18 antibodies had similar activity.

As chimeric E18 neutralization activity was lower than the parental mouse antibody, a second recombinant chimeric E18 was generated by shortening the VL sequence. The new E18-derived VL sequence, VL2, was provided in Table 4 (SEQ ID NO: 15). Expression of the new recombinant chimeric E18 antibody was completed in plant cells. The parental mouse E18 and both chimeric E18 antibodies were tested for their ability to neutralize EV71 in cell culture using Vero cells (FIG. 8). Antibodies (Ab) were diluted and various concentrations, as shown on the x-axis, were assayed. For each antibody concentration, the percent reduction in viral plaques was determined (y-axis). The parental mouse E18 demonstrated the best neutralization activity at the lowest concentrations. Both chimeric E18 antibodies neutralized EV71 to a similar extent as illustrated by the nearly overlapping curves.

Figure 9:
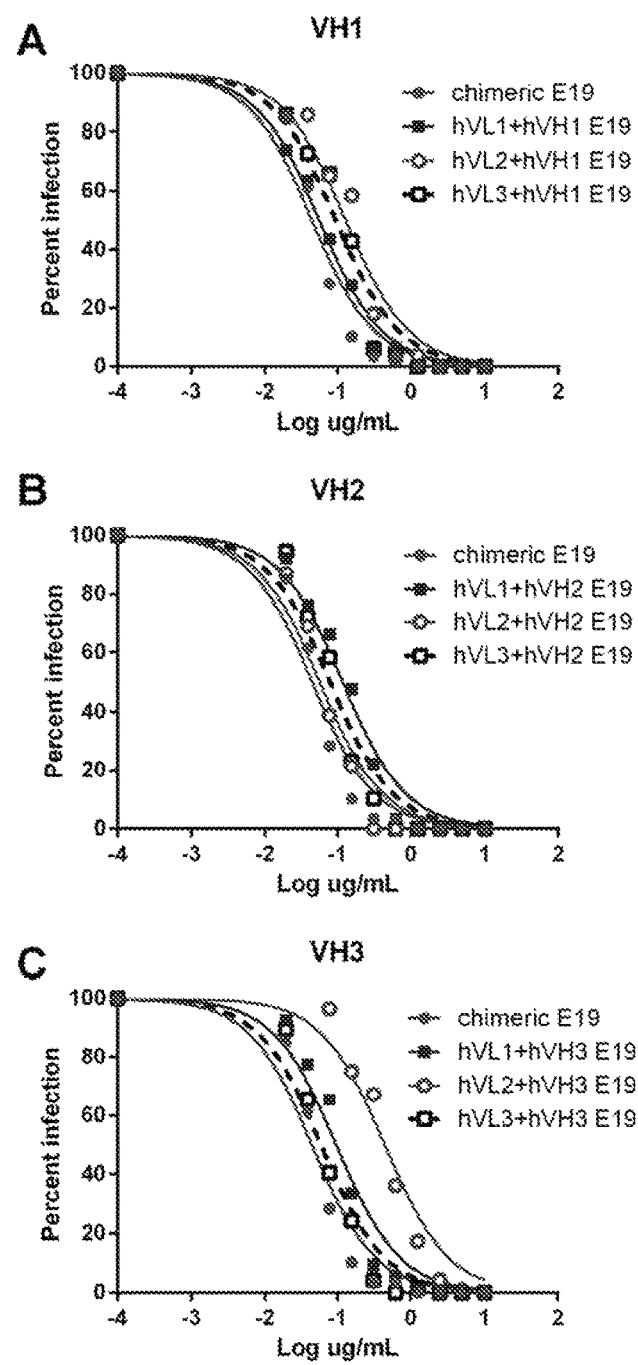
FIG. 9 includes three graphs showing the neutralization of EV71 by recombinant humanized E19-derived antibodies.

As recombinant chimeric E19 was the most promising recombinant neutralizing antibody, further genetic manipulations were done within the variable framework regions of VL and VH2 (SEQ ID NOs: 3 and 5) to generate recombinant fully humanized E19 monoclonal antibodies. Three versions of VL and three versions of VH2 were initially created by modeling human antibody framework and introducing specific amino acid substitutions into the mouse E19 VL and VH2 framework regions. The six new fully humanized E19 VL- and VH2-derived sequences are provided in Table 4 (SEQ ID NOs: 16, 17, 18, 19, 20 and 21) and are labeled as hVL1, hVL2, hVL3, hVH1, hVH2 and hVH3 to distinguish them from the parental mouse VL and VH2 sequences (SEQ ID NOs: 3 and 5). Nine different combinations of E19-derived hVL and hVH were expressed as whole human IgG antibodies and each was tested for EV71 neutralization activity. As shown in FIG. 9, all nine recombinant fully humanized E19 monoclonal antibodies were capable of neutralizing EV71.

TABLE 8

Recombinant humanized E19 antibody neutralization profiles.

| Antibody | SEQ ID NOs | IC50 (#1) ng/mL | IC50 (#2) ng/mL | Average IC50 (ng/mL) |
|---|---|---|---|---|
| Chimeric E19 | 3, 5 | 44.73 | 21.86 | 33.295 |
| hVL1 + hVH1 E19 | 16, 19 | 56.54 | 121.8 | 89.17 |
| hVL2 + hVH1 E19 | 17, 19 | 130 | 132 | 131 |
| hVL3 + hVH1 E19 | 18, 19 | 95.12 | 96.67 | 95.895 |
| hVL1 + hVH2 E19 | 16, 20 | 117.5 | 121.3 | 119.4 |
| hVL2 + hVH2 E19 | 17, 20 | 56.95 | 43.41 | 50.18 |
| hVL3 + hVH2 E19 | 18, 20 | 78.85 | 60.8 | 69.825 |
| hVL1 + hVH3 E19 | 16, 21 | 96.5 | 82.63 | 89.565 |
| hVL2 + hVH3 E19 | 17, 21 | 444.2 | 48.2 | 246.2 |
| hVL3 + hVH3 E19 | 18, 21 | 59.74 | 52.4 | 56.07 |

Further when IC50s were extrapolated for each antibody, the three recombinant fully human antibodies with the best neutralization profile were hVL2+hVH2, hVL3+hVH3 and hVL3+hVH2 (SEQ ID NOs: 17, 18 20 and 21). Importantly, the IC50s of the three best recombinant fully human E19 antibodies were similar to the IC50s observed for the chimeric E19 VL+VH2 antibody (Tables 7 and 8) and better than the parental mouse E19 antibody (Table 7). As hVL2+ hVH2 consistently demonstrated the lowest IC50, it represents the best candidate for a therapeutic antibody as it is fully humanized and highly neutralizing. Interestingly, further examination of the hVH2 sequence revealed that the framework 3 region lacks an arginine residue found in many human VH framework 3 regions. In an effort to further optimize the therapeutic potential of the hVL2+hVH2 E19 antibody a seventh sequence was generated that was derived from hVH2 but included the additional arginine residue in the correct position. This new sequence was provided in Table 4 (SEQ ID NO: 22) and was labeled hVH4. Expression of the new hVL2+hVH4 E19 antibody is complete and assessing antibody function is underway.

In an effort to reduce the cost of therapeutic antibody manufacturing, expression of the recombinant antibodies was piloted in *Nicotiana benthamiana* plant cells. Specifically, chimeric VL2+VH E18 antibody (SEQ ID NOs: 15 and 2) and the recombinant fully humanized hVL2+hVH4 E19 antibody (SEQ ID NOs: 17 and 22) were chosen for pilot plant cell expression. Plant transformation and expression was done as described in the methods and currently, over 300 milligrams of each recombinant antibody have been purified. Functional assays assessing neutralization activity have been completed for the second E18 chimeric (FIG. 8) and are underway for humanized E19. Based on the results for the second chimeric E18 plant cells represent a viable manufacturing platform for recombinant antibodies provided for in this application.

REFERENCES

1. Cole et al., (1985) *Monoclonal Antibodies and Cancer Therapy* Alan R. Liss, Inc., pp 77-96
2. Cote et al., (1983) *Proc. Nat. Acad. Sci. U.S.A.*, 80: 2026-2030
3. Kiener, T., Q. Jia, et al., (2012). "Characterization and specificity of the linear epitope of the *enterovirus* 71 VP2 protein." *Virology journal* 9: 55.
4. Li, X., C. Mao, et al., (2009). "Generation of neutralizing monoclonal antibodies against *Enterovirus* 71 using synthetic peptides." *Biochemical and biophysical research communications* 390(4): 1126-1128.
5. Lim, X., Q. Jia, et al., (2012). "Characterization of an isotype-dependent monoclonal antibody against linear neutralizing epitope effective for prophylaxis of *enterovirus* 71 infection." *PloS one* 7(1).
6. Liu, C.-C., A.-H. Chou, et al., (2011). "Identification and characterization of a cross-neutralization epitope of *Enterovirus* 71." *Vaccine* 29(26): 4362-4372.
7. Morrison et al., (1984) *Proc. Nat. Acad. Sci. U.S.A.*, 81(21): 6851-5
8. http://www.piercenet.com/product/fab-preparation-kits, 10 Dec. 2013.
9. Plevka et al., (2012) *Acta Crystallogr D Biol Crystallogr* 68: 1217-1222.
10. Qiu X., et al., (2014) "Reversion of advanced Ebola virus disease in nonhuman primates with ZMapp" *Nature* 514(7520): 47-53.
11. Zhang, J., M. Dong, et al., (2012). "Antigenic characteristics of the complete and truncated capsid protein VP1 of *enterovirus* 71." *Virus research* 167(2): 337-342.

The invention claimed is:

1. An isolated antibody or epitope-binding fragment thereof that specifically binds to at least one conformational (non-linear) epitope of *enterovirus* 71 (EV71), wherein the antibody comprises at least one variable light chain and at least one variable heavy chain, wherein the variable light chain comprises an amino acid sequence comprising the amino acid sequence set forth in SEQ ID NO: 1 or 15, and wherein the variable heavy chain comprises an amino acid sequence comprising the amino acid sequence set forth in SEQ ID NO: 2, wherein the antibody or fragment thereof is neutralizing.

2. The isolated antibody or fragment thereof of claim 1, wherein the antibody is a monoclonal mouse, human, humanized or chimeric antibody.

3. The isolated antibody or fragment thereof of claim 1 for use in EV71 vaccine process control, candidate EV71 vaccine purification or determining EV71 antibody potency standards.

4. The isolated antibody or fragment thereof of claim 1 for use in treatment of EV71 infection and/or at least one EV71-linked disease selected from the group consisting of aseptic meningitis, encephalitis, cranial nerve palsies, Guillain-Barre syndrome, poliomyelitis-like syndrome, brainstem encephalitis, herpangina, and Hand, Foot and Mouth disease.

5. A method of treating at least one of an EV71-infection and at least one EV-linked disease selected from the group consisting of aseptic meningitis, encephalitis, cranial nerve palsies, Guillain-Barre syndrome, poliomyelitis-like syndrome, brainstem encephalitis, herpangina, and Hand, Foot and Mouth disease, the method comprising administering to a subject the antibody or epitope-binding fragment thereof of claim 1.

6. An isolated nucleic acid molecule encoding
   (a) at least one variable light chain of the antibody or epitope-binding fragment thereof of claim 1, wherein the variable light chain comprises an amino acid sequence selected from the amino acid sequence set forth in SEQ ID NO: 1 and the amino acid sequence set forth in SEQ ID NO: 15; and
   (b) at least one variable heavy chain of the antibody or epitope-binding fragment thereof of claim 1, wherein the variable heavy chain comprises the amino acid sequence set forth in SEQ ID NO: 2.

7. The isolated nucleic acid molecule of claim 6, wherein the nucleic acid sequence encoding the variable light chain or epitope-binding fragment thereof in (a) has at least 90% sequence identity to the nucleic acid sequence set forth in SEQ ID NO: 8 or SEQ ID NO: 23 or to the portion thereof encoding the epitope-binding fragment; and wherein the nucleic acid sequence encoding the variable heavy chain in (b) has at least 90% sequence identity to the nucleic acid sequence set forth in SEQ ID NO: 9 or to the portion thereof encoding the epitope-binding fragment.

8. The isolated nucleic acid molecule of claim 7, comprising:
   (a) the nucleic acid sequence set forth in SEQ ID NO: 8 and/or SEQ ID NO: 23; and
   (b) the nucleic acid sequence set forth in SEQ ID NO: 9.

9. An expression vector comprising at least one isolated nucleic acid molecule defined in any one of claims 6 to 8.

* * * * *

```
                        SEQUENCE LISTING

<160> NUMBER OF SEQ ID NOS: 30

<210> SEQ ID NO 1
<211> LENGTH: 108
<212> TYPE: PRT
<213> ORGANISM: Artificial Sequence
<220> FEATURE:
<223> OTHER INFORMATION: Antibody E18 VL Chain

<400> SEQUENCE: 1

Asp Ile Lys Met Thr Gln Ser Pro Ser Met Tyr Ala Ser Leu Gly
1               5                   10                  15

Glu Arg Val Thr Ile Thr Cys Lys Ala Ser Gln Asp Ile Lys Ser Tyr
                20                  25                  30

Leu Ser Trp Tyr Gln Gln Lys Pro Trp Lys Ser Pro Lys Thr Leu Ile
            35                  40                  45

Tyr Tyr Ala Lys Asn Leu Ala Asp Gly Val Pro Ser Arg Phe Ser Gly
        50                  55                  60

Ser Gly Phe Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Tyr
                85                  90                  95

Thr Phe Gly Ser Gly Thr Lys Leu Glu Ile Lys Arg
                100                 105

<210> SEQ ID NO 2
<211> LENGTH: 120
<212> TYPE: PRT
<213> ORGANISM: Artificial Sequence
<220> FEATURE:
<223> OTHER INFORMATION: Antibody E18 VH Chain

<400> SEQUENCE: 2

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Arg Tyr
                20                  25                  30

Gly Met Ser Trp Val Lys Gln Ala Pro Gly Lys Gly Leu Lys Trp Met
            35                  40                  45

Gly Trp Ile Asn Thr Tyr Ser Gly Val Pro Thr Tyr Ala Asp Asp Phe
        50                  55                  60
```

```
Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Arg Gly Tyr Ser Asn Tyr Tyr Pro Met Asp Phe Trp Gly Gln
            100                 105                 110

Gly Thr Ser Val Thr Val Ser Ser
            115                 120
```

<210> SEQ ID NO 3
<211> LENGTH: 112
<212> TYPE: PRT
<213> ORGANISM: Artificial Sequence
<220> FEATURE:
<223> OTHER INFORMATION: Antibody E19 VL Chain

<400> SEQUENCE: 3

```
Asn Ile Met Met Thr Gln Ser Pro Ser Ser Leu Ala Val Ser Ala Gly
  1               5                  10                  15

Gly Lys Val Thr Met Ser Cys Lys Ser Ser Gln Ser Val Leu Tyr Ser
             20                  25                  30

Ser Asn Gln Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys His Gln
                 85                  90                  95

Tyr Leu Ser Ser Trp Thr Phe Gly Gly Gly Thr Lys Leu Glu Ile Lys
            100                 105                 110
```

<210> SEQ ID NO 4
<211> LENGTH: 122
<212> TYPE: PRT
<213> ORGANISM: Artificial Sequence
<220> FEATURE:
<223> OTHER INFORMATION: Antibody E19 VH1 Chain

<400> SEQUENCE: 4

```
Glu Val Met Leu Val Glu Ser Gly Gly Gly Leu Val Lys Pro Gly Gly
  1               5                  10                  15

Ser Leu Gln Leu Ser Cys Ala Ala Ser Gly Phe Thr Phe Ser Asp Tyr
             20                  25                  30

Ala Met Ser Trp Val Arg Gln Thr Ala Glu Thr Arg Leu Glu Trp Val
             35                  40                  45

Ala Thr Ile Ser Asp Gly Gly Ser His Thr Tyr Tyr Pro Asp Ser Val
 50                  55                  60

Arg Gly Arg Phe Thr Ile Ser Arg Asp Asn Ala Lys Lys Ala Leu Tyr
 65                  70                  75                  80

Leu Glu Met Ser Ser Leu Lys Ser Glu Asp Thr Ala Met Tyr Tyr Cys
                 85                  90                  95

Gly Arg Arg Ala Gly Arg Tyr Asp Glu Arg Asp Ala Met Asp Tyr Trp
            100                 105                 110

Gly Gln Gly Thr Thr Val Thr Val Ser Ser
            115                 120
```

```
<210> SEQ ID NO 5
<211> LENGTH: 119
<212> TYPE: PRT
<213> ORGANISM: Artificial Sequence
<220> FEATURE:
<223> OTHER INFORMATION: Antibody E19 VH2 Chain

<400> SEQUENCE: 5

Ser Asp Val Gln Leu Gln Glu Ser Gly Pro Gly Leu Val Lys Pro Ser
1               5                   10                  15

Gln Ser Leu Ser Leu Thr Cys Ser Val Thr Gly Tyr Ser Ile Thr Ser
            20                  25                  30

Gly Phe Tyr Leu Asn Trp Ile Arg Gln Phe Pro Gly Asn Lys Leu Glu
        35                  40                  45

Trp Met Gly Tyr Ile Asn Tyr Gly Gly Ser Ile Asn Tyr Asn Pro Ser
    50                  55                  60

Leu Lys Ser Arg Ile Ser Ile Thr Arg Asp Thr Ser Lys Asn Gln Phe
65                  70                  75                  80

Phe Leu Arg Leu Asn Ser Val Thr Ala Glu Asp Thr Ala Thr Tyr Tyr
                85                  90                  95

Cys Ala Thr Met Pro Asn Ser Trp Tyr Phe Asp Val Trp Gly Thr Gly
            100                 105                 110

Thr Thr Val Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: Antibody E20 VL Chain

<400> SEQUENCE: 6

Ser Ile Val Met Thr Gln Thr Pro Lys Phe Leu Pro Val Ser Ala Gly
1               5                   10                  15

Asp Arg Val Thr Met Thr Cys Lys Ala Ser Gln Ser Val Gly Asn Asn
            20                  25                  30

Val Ala Trp Tyr Gln Gln Lys Ser Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Ser Gly Thr Asp Phe Thr Phe Thr Ile Ser Ser Val Gln Val
65                  70                  75                  80

Glu Asp Leu Ala Val Tyr Phe Cys Gln Gln His Tyr Ser Ser Pro Pro
                85                  90                  95

Thr Phe Gly Ala Gly Thr Lys Leu Glu Leu Lys
            100                 105

<210> SEQ ID NO 7
<211> LENGTH: 123
<212> TYPE: PRT
<213> ORGANISM: Artificial Sequence
<220> FEATURE:
<223> OTHER INFORMATION: Antibody E20 VH Chain

<400> SEQUENCE: 7

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Asn Ile Tyr
            20                  25                  30
```

```
Ala Met Ser Trp Val Arg Gln Thr Pro Glu Lys Arg Leu Glu Trp Val
             35                  40                  45

Ala Thr Ile Ser Asp Gly Gly Ser Tyr Thr Tyr Tyr Pro Asp Asn Val
 50                  55                  60

Lys Gly Arg Phe Thr Ile Ser Arg Asp Asn Ala Lys Asn Asn Leu Tyr
 65                  70                  75                  80

Leu Gln Met Ser His Leu Lys Ser Glu Asp Thr Ala Met Tyr Tyr Cys
             85                  90                  95

Val Arg Asp Arg Gly Asn Tyr Tyr Ser Arg Ala Phe Pro Tyr Ala Tyr
            100                 105                 110

Trp Gly Gln Gly Thr Leu Val Thr Val Ser Ala
            115                 120
```

<210> SEQ ID NO 8
<211> LENGTH: 324
<212> TYPE: DNA
<213> ORGANISM: Artificial Sequence
<220> FEATURE:
<223> OTHER INFORMATION: Antibody E18 VL Chain

<400> SEQUENCE: 8

```
gacatcaaga tgacccagtc tccatcctcc atgtatgcat cgctgggaga gagagtcact    60
atcacttgca aggcgagtca ggacattaaa agctatttaa gctggtacca gcagaaacca   120
tggaaatctc ctaagaccct gatctattat gcaaaaaact ggcagatgg ggtcccatca    180 agattcagtg gcagtggatt tgggcaagat tattctctaa ccatcagcag cctggagtct   240
gacgatacag caactyatta ctgtctacag catggtgaga gcccgtatac gttcggatcg   300
gggaccaaac tggaaataaa acgg                                          324
```

<210> SEQ ID NO 9
<211> LENGTH: 360
<212> TYPE: DNA
<213> ORGANISM: Artificial Sequence
<220> FEATURE:
<223> OTHER INFORMATION: Antibody E18 VH Chain

<400> SEQUENCE: 9

```
cagatccagt tggtacagtc tggacctgag ctgaagaagc ctggagagac agtcaagatc    60
tcctgcaagg cttctggata taccttcaca aggtatggaa tgagctgggt gaaacaggct   120
ccaggaaagg gtttaaagtg gatgggctgg ataaacacct actctggagt gccaacatat   180
gctgacgact caagggacg gtttgccttc tctttggaaa cctctgccag cactgcctat   240
ttgcagatca acaacctcaa aaatgaggac acggctacat atttctgtgc aagaagggg   300 tatagtaact attatcctat ggacttctgg ggtcaaggaa cctcagtcac cgtctcctca   360
```

<210> SEQ ID NO 10
<211> LENGTH: 336
<212> TYPE: DNA
<213> ORGANISM: Artificial Sequence
<220> FEATURE:
<223> OTHER INFORMATION: Antibody E19 VL Chain

<400> SEQUENCE: 10

```
aacattatga tgacacagtc gccatcatct ctggctgtgt ctgcaggagg aaaggtcact    60
atgagctgta gtccagtca aagtgtttta tacagttcaa atcagaagaa ctacttggcc   120
tggtaccagc agaaaccagg gcagtctcct aaactactga tctactgggc atccactagg   180
gaatctggtg tccctgatcg cttcacaggc agtggatctg ggacagattt tactcttacc   240
```

```
atcagcagtg tacaagctga agacctggca gtttattact gtcatcaata cctctcctcg   300
tggacgttcg gtggaggcac caagctggaa atcaaa                             336
```

<210> SEQ ID NO 11
<211> LENGTH: 366
<212> TYPE: DNA
<213> ORGANISM: Artificial Sequence
<220> FEATURE:
<223> OTHER INFORMATION: Antibody E19 VH1 Chain

<400> SEQUENCE: 11

```
gaagtgatgc tggtggagtc tgggggaggc ttagtgaagc ctggagggtc cctccaactc    60
tcctgtgcag cctctggatt cacgttcagt gactatgcca tgtcttgggt tcgccagact   120
gcggagacga ggctgagtg gtcgcaacc atcagtgatg gtggtagtca cacctactat     180
ccagacagtg tgaggggacg gttcaccatc tccagagaca tgccaagaa ggccctgtac    240 ctggaaatga gcagtctgaa gtctgaggac acggccatgt attactgtgg aagacgggcg   300
gggaggtacg atgagagaga tgctatggac tactggggtc aaggaaccac agtcaccgtc   360
tcctca                                                              366
```

<210> SEQ ID NO 12
<211> LENGTH: 357
<212> TYPE: DNA
<213> ORGANISM: Artificial Sequence
<220> FEATURE:
<223> OTHER INFORMATION: Antibody E19 VH2 Chain

<400> SEQUENCE: 12

```
tctgatgtac agcttcagga gtcaggacct ggcctcgtga aacttctca gtctctgtct     60 ctcacctgct ctgtcactgg ctactccatc accagtggtt tttacttaaa ctggatccgg   120
cagtttccag gaaacaaact ggaatggatg gctacataa actacggtgg tagcattaac    180
tacaacccat ctctcaaaag tcgcatctcc atcactcgtg acacatctaa gaaccagttt   240
ttcctgaggt tgaattctgt gactgctgag gacacagcca catattactg tgcaaccatg   300
cctaactcct ggtacttcga tgtctggggc acagggacca cggtcaccgt ctcctca      357
```

<210> SEQ ID NO 13
<211> LENGTH: 321
<212> TYPE: DNA
<213> ORGANISM: Artificial Sequence
<220> FEATURE:
<223> OTHER INFORMATION: Antibody E20 VL Chain

<400> SEQUENCE: 13

```
agtattgtga tgacccagac tcccaaattc ctgcctgtat cagcaggaga cagggttacc    60
atgacctgca aggccagtca gagtgtgggt aataatgtag cctggtacca acagaagtca   120
ggacagtctc ctaaactgct gatatactat gcatccaatc gctacactgg agtccctgat   180
cgcttcactg gcagtggatc tgggacagat ttcactttca ccatcagcag tgtgcaggtt   240
gaagacctgg cagtttattt ctgtcagcag cattatagct ctcctcccac gttcggtgct   300
gggaccaagc tggagctgaa a                                             321
```

<210> SEQ ID NO 14
<211> LENGTH: 369
<212> TYPE: DNA
<213> ORGANISM: Artificial Sequence
<220> FEATURE:
<223> OTHER INFORMATION: Antibody E20 VH Chain

```
<400> SEQUENCE: 14
gaagtgcagc tggtggagtc tgggggaggc ttagtgaagc ctggagggtc cctgaaactc    60
tcctgtgcag cctctggatt cactttcaac atctatgcca tgtcttgggt tcgccagact   120
ccggaaaaga ggctggagtg gtcgcaacc attagtgatg gtggtagtta tacctactat   180
ccagacaatg taaagggccg attcaccatc tccagagaca atgccaagaa caacctgtac   240
ctgcaaatga ccatctgaa gtctgaggac acagccatgt attactgtgt aagagatcga   300
ggaaattact acagtagagc gttcccgtat gcttactggg gccaagggac tctggtcact   360
gtctctgca                                                           369

<210> SEQ ID NO 15
<211> LENGTH: 107
<212> TYPE: PRT
<213> ORGANISM: Artificial Sequence
<220> FEATURE:
<223> OTHER INFORMATION: Antibody E18 VL2 Chain derived from SEQ ID NO:
      1

<400> SEQUENCE: 15

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Tyr Gln Gln Lys Pro Trp Lys Ser Pro Lys Thr Leu Ile
        35                  40                  45

Tyr Tyr Ala Lys Asn Leu Ala Asp Gly Val Pro Ser Arg Phe Ser Gly
    50                  55                  60

Ser Gly Phe Gly Gln Asp Tyr Ser Leu Thr Ile Ser Ser Leu Glu Ser
65                  70                  75                  80

Asp Asp Thr Ala Thr Tyr Tyr Cys Leu Gln His Gly Glu Ser Pro Tyr
                85                  90                  95

Thr Phe Gly Ser Gly Thr Lys Leu Glu Ile Lys
            100                 105

<210> SEQ ID NO 16
<211> LENGTH: 112
<212> TYPE: PRT
<213> ORGANISM: Artificial Sequence
<220> FEATURE:
<223> OTHER INFORMATION: Antibody E19 humanized VL1 Chain derived from
      SEQ ID NO: 3

<400> SEQUENCE: 16

Asn Ile Met Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Ser Trp Thr Phe Gly Gln Gly Thr Lys Val Glu Ile Lys
            100                 105                 110
```

```
<210> SEQ ID NO 17
<211> LENGTH: 112
<212> TYPE: PRT
<213> ORGANISM: Artificial Sequence
<220> FEATURE:
<223> OTHER INFORMATION: Antibody E19 humanized VL2 Chain derived from
      SEQ ID NO: 3

<400> SEQUENCE: 17

Asn Ile Met Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Ser Ser Trp Thr Phe Gly Gly Gly Thr Lys Val Glu Ile Lys
            100                 105                 110

<210> SEQ ID NO 18
<211> LENGTH: 112
<212> TYPE: PRT
<213> ORGANISM: Artificial Sequence
<220> FEATURE:
<223> OTHER INFORMATION: Antibody E19 humanized VL3 Chain derived from
      SEQ ID NO: 3

<400> SEQUENCE: 18

Asn Ile Met Met Thr Gln Ser Pro Asp Ser Leu Ala Leu Ser Leu Gly
1               5                   10                  15

Glu Arg Ala Thr Ile Asn Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Leu Tyr Tyr Cys His Gln
                85                  90                  95

Tyr Leu Ser Ser Trp Thr Phe Gly Gly Gly Thr Lys Val Glu Ile Lys
            100                 105                 110

<210> SEQ ID NO 19
<211> LENGTH: 118
<212> TYPE: PRT
<213> ORGANISM: Artificial Sequence
<220> FEATURE:
<223> OTHER INFORMATION: Antibody E19 humanized VH1 Chain derived from
      SEQ ID NO: 5

<400> SEQUENCE: 19

Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30
```

Phe Tyr Leu Asn Trp Ile Arg Gln His Pro Cys Lys Gly Leu Glu Trp
            35                  40                  45

Ile Gly Tyr Ile Asn Tyr Gly Gly Ser Ile Asn Tyr Asn Pro Ser Leu
 50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Thr Met Pro Asn Ser Trp Tyr Phe Asp Val Trp Gly Arg Gly Thr
            100                 105                 110

Leu Val Thr Val Ser Ser
        115

<210> SEQ ID NO 20
<211> LENGTH: 118
<212> TYPE: PRT
<213> ORGANISM: Artificial Sequence
<220> FEATURE:
<223> OTHER INFORMATION: Antibody E19 humanized VH2 Chain derived from
      SEQ ID NO: 5

<400> SEQUENCE: 20

Asp Val Gln Leu Gln Glu Ser Gly Pro Gly Leu Val Lys Pro Ser Gln
 1               5                  10                  15

Thr Leu Ser Leu Thr Cys Thr Val Ser Gly Tyr Ser Ile Thr Ser Gly
             20                  25                  30

Phe Tyr Leu Asn Trp Ile Arg Gln His Pro Gly Lys Lys Leu Glu Trp
            35                  40                  45

Ile Gly Tyr Ile Asn Tyr Gly Gly Ser Ile Asn Tyr Asn Pro Ser Leu
 50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Thr Met Pro Asn Ser Trp Tyr Phe Asp Val Trp Gly Thr Gly Thr
            100                 105                 110

Leu Val Thr Val Ser Ser
        115

<210> SEQ ID NO 21
<211> LENGTH: 118
<212> TYPE: PRT
<213> ORGANISM: Artificial Sequence
<220> FEATURE:
<223> OTHER INFORMATION: Antibody E19 humanized VH3 Chain derived from
      SEQ ID NO: 5

<400> SEQUENCE: 21

Glu Val Gln Leu Val Glu Ser Gly Pro Gly Leu Val Lys Pro Ser Gln
 1               5                  10                  15

Thr Leu Ser Leu Thr Cys Thr Val Ser Gly Tyr Ser Ile Thr Ser Gly
             20                  25                  30

Phe Tyr Leu Asn Trp Val Arg Gln His Pro Gly Lys Lys Leu Glu Trp
            35                  40                  45

Ile Gly Tyr Ile Asn Tyr Gly Gly Ser Ile Asn Tyr Asn Pro Ser Leu
 50                  55                  60

Lys Ser Arg Val Ser Ile Ser Arg Asp Thr Ser Lys Asn Gln Phe Ser
 65                  70                  75                  80

```
Leu Lys Leu Thr Ser Val Thr Ala Ala Asp Thr Ala Val Tyr Tyr Cys
            85                  90                  95

Ala Thr Met Pro Asn Ser Trp Tyr Phe Asp Val Trp Gly Thr Gly Thr
           100                 105                 110

Leu Val Thr Val Ser Ser
        115

<210> SEQ ID NO 22
<211> LENGTH: 119
<212> TYPE: PRT
<213> ORGANISM: Artificial Sequence
<220> FEATURE:
<223> OTHER INFORMATION: Antibody E19 humanized VH4 Chain derived from
      SEQ ID NO: 20

<400> SEQUENCE: 22

Asp Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Phe Tyr Leu Asn Trp Ile Arg Gln His Pro Gly Lys Lys Leu Glu Trp
            35                  40                  45

Ile Gly Tyr Ile Asn Tyr Gly Gly Ser Ile Asn Tyr Asn Pro Ser Leu
     50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Thr Met Pro Asn Ser Trp Tyr Phe Asp Val Trp Gly Thr Gly
           100                 105                 110

Thr Leu Val Thr Val Ser Ser
        115

<210> SEQ ID NO 23
<211> LENGTH: 321
<212> TYPE: DNA
<213> ORGANISM: Artificial Sequence
<220> FEATURE:
<223> OTHER INFORMATION: Antibody E18 VL2 Chain derived from SEQ ID NO:
      1

<400> SEQUENCE: 23
gacatcaaga tgacccagtc tccatcctcc atgtatgcat cgctgggaga gagagtcact      60
atcacttgca aggcgagtca ggacattaaa agctatttaa gctggtacca gcagaaacca     120
tggaaatctc ctaagaccct gatctattat gcaaaaaact ggcagatgg  ggtcccatca     180 agattcagtg gcagtggatt tgggcaagat tattctctaa ccatcagcag cctggagtct     240
gacgatacag caacttatta ctgtctacag catggtgaga gcccgtatac gttcggatcg     300
gggaccaaac tggaaataaa a                                               321

<210> SEQ ID NO 24
<211> LENGTH: 336
<212> TYPE: DNA
<213> ORGANISM: Artificial Sequence
<220> FEATURE:
<223> OTHER INFORMATION: Antibody E19 humanized VL1 Chain derived from
      SEQ ID NO: 3
```

```
<400> SEQUENCE: 24
aatatcatga tgacccagtc ccccgactcc ctggccgtgt ctctgggaga gagagccacc      60
atcaactgca agtcctccca gtccgtgctg tactcctcca accagaagaa ctacctggcc     120
tggtatcagc agaagcccgg ccagcctccc aagctgctga tctactgggc ctccacccgg     180
gaatctggcg tgcccgatag attctccggc tccggctctg gcaccgactt taccctgacc     240
atcagctccc tgcaggccga ggatgtggcc gtgtactact gccaccagta cctgtcctct     300
tggaccttcg gccagggcac caaggtggaa atcaag                               336

<210> SEQ ID NO 25
<211> LENGTH: 336
<212> TYPE: DNA
<213> ORGANISM: Artificial Sequence
<220> FEATURE:
<223> OTHER INFORMATION: Antibody E19 humanized VL2 Chain derived from
      SEQ ID NO: 3

<400> SEQUENCE: 25
aatatcatga tgacccagtc ccccgactcc ctggccgtgt ctctgggaga gagagccacc      60
atcaactgca agtcctccca gtccgtgctg tactcctcca accagaagaa ctacctggcc     120
tggtatcagc agaagcccgg ccagtcccct aagctgctga tctactgggc ctccacccgg     180
gaatctggcg tgcccgatag attctccggc tccggctctg gcaccgactt taccctgacc     240
atcagctccc tgcaggccga ggatgtggcc gtgtactact gccaccagta cctgtcctct     300
tggaccttcg gcggaggcac caaggtggaa atcaag                               336

<210> SEQ ID NO 26
<211> LENGTH: 336
<212> TYPE: DNA
<213> ORGANISM: Artificial Sequence
<220> FEATURE:
<223> OTHER INFORMATION: Antibody E19 humanized VL3 Chain derived from
      SEQ ID NO: 3

<400> SEQUENCE: 26
aatatcatga tgacccagtc ccccgactcc ctggccctgt ctctgggaga gagagccacc      60
atcaactgca agtcctccca gtccgtgctg tactcctcca accagaagaa ctacctggcc     120
tggtatcagc agaagcccgg ccagtcccct aagctgctga tctactgggc ctcctcccgg     180
gaatctggcg tgcccgatag attctccggc tccggctctg gcaccgactt taccctgacc     240
atcagctccc tgcaggccga ggatgtggcc ctgtactact gccaccagta cctgtcctct     300
tggaccttcg gcggaggcac caaggtggaa atcaag                               336

<210> SEQ ID NO 27
<211> LENGTH: 354
<212> TYPE: DNA
<213> ORGANISM: Artificial Sequence
<220> FEATURE:
<223> OTHER INFORMATION: Antibody E19 humanized VH1 Chain derived from
      SEQ ID NO: 5

<400> SEQUENCE: 27
gatgtgcagc tgcaggaatc tggccctggc ctcgtgaagc cttcccagac cctgtctctg      60
acctgcaccg tgtccggcta ctccatcacc tccggcttct acctgaactg gatccggcag     120
```

-continued

```
cacccctgca agggcctgga atggatcggc tacatcaact acggcggctc tatcaactac      180
aaccccagcc tgaagtccag agtgaccatc tcccgggaca cctccaagaa ccagttctcc      240
ctgaagctgt cctccgtgac cgccgctgat accgccgtgt actactgcgc taccatgccc      300
aacagctggt acttcgacgt gtggggcaga ggcaccctcg tgaccgtgtc atct            354
```

<210> SEQ ID NO 28
<211> LENGTH: 354
<212> TYPE: DNA
<213> ORGANISM: Artificial Sequence
<220> FEATURE:
<223> OTHER INFORMATION: Antibody E19 humanized VH2 Chain derived from
      SEQ ID NO: 5

<400> SEQUENCE: 28

```
gatgtgcagc tgcaggaatc tggccctggc ctcgtgaagc cttcccagac cctgtctctg      60
acctgcaccg tgtccggcta ctccatcacc tccggcttct acctgaactg gatccggcag     120
caccccggca agaaactgga atggatcggc tacatcaact acggcggctc tatcaactac     180
aaccccagcc tgaagtccag agtgaccatc tcccgggaca cctccaagaa ccagttctcc     240
ctgaagctgt cctccgtgac cgccgctgat accgccgtgt actactgcgc taccatgccc     300
aacagctggt acttcgacgt gtggggcacc ggcaccctcg tgacagtgtc atct            354
```

<210> SEQ ID NO 29
<211> LENGTH: 354
<212> TYPE: DNA
<213> ORGANISM: Artificial Sequence
<220> FEATURE:
<223> OTHER INFORMATION: Antibody E19 humanized VH3 Chain derived from
      SEQ ID NO: 5

<400> SEQUENCE: 29

```
gaagtgcagc tggtggaatc tggccctggc ctcgtgaagc cttcccagac cctgtctctg      60
acctgcaccg tgtccggcta ctccatcacc tccggcttct acctgaactg ggtgcgacag     120
caccccggca agaaactgga atggatcggc tacatcaact acggcggctc tatcaactac     180
aaccccagcc tgaagtcccg ggtgtccatc tcccgggaca cctccaagaa ccagttctcc     240
ctgaagctga cctccgtgac cgccgctgat accgccgtgt actactgcgc taccatgccc     300
aacagctggt acttcgacgt gtggggcacc ggcaccctcg tgacagtgtc atct            354
```

<210> SEQ ID NO 30
<211> LENGTH: 357
<212> TYPE: DNA
<213> ORGANISM: Artificial Sequence
<220> FEATURE:
<223> OTHER INFORMATION: Antibody E19 humanized VH4 Chain derived from
      SEQ ID NO: 20

<400> SEQUENCE: 30

```
gatgtgcagc tgcaggaatc tggccctggc ctcgtgaagc cttcccagac cctgtctctg      60
acctgcaccg tgtccggcta ctccatcacc tccggcttct acctgaactg gatccggcag     120
caccccggca agaaactgga atggatcggc tacatcaact acggcggctc tatcaactac     180
aaccccagcc tgaagtccag agtgaccatc tcccgggaca cctccaagaa ccagttctcc     240
ctgaagctgt cctccgtgac cgccgctgat accgccgtgt actactgcgc tcgcaccatg     300
cccaacagct ggtacttcga cgtgtggggc accggcaccc tcgtgacagt gtcatct        357
```